US012633415B2

(12) United States Patent
Barrett et al.

(10) Patent No.: US 12,633,415 B2
(45) Date of Patent: May 19, 2026

(54) PRE-EMPTIVE ASTHMA RISK NOTIFICATIONS BASED ON MEDICAMENT DEVICE MONITORING

(71) Applicant: Reciprocal Labs Corporation, Madison, WI (US)

(72) Inventors: Meredith A. Barrett, Redwood City, CA (US); Mike Lohmeier, Sun Prairie, WI (US); Shannon M. Hamilton, Berkeley, CA (US); Michael J. Tuffli, Kentfield, CA (US); Dmitry Stupakov, Cupertino, CA (US); Christopher Hogg, San Francisco, CA (US); John David Van Sickle, Oregon, WI (US)

(73) Assignee: ResMed Inc., San Diego, CA (US)

( * ) Notice: Subject to any disclaimer, the term of this patent is extended or adjusted under 35 U.S.C. 154(b) by 0 days.

(21) Appl. No.: 17/540,186

(22) Filed: Dec. 1, 2021

(65) Prior Publication Data

US 2022/0093262 A1 Mar. 24, 2022

Related U.S. Application Data

(63) Continuation of application No. 15/724,968, filed on Oct. 4, 2017, now Pat. No. 11,195,622.

(51) Int. Cl.
*G16H 50/30* (2018.01)
*G16H 10/65* (2018.01)
(Continued)

(52) U.S. Cl.
CPC ............. *G16H 50/30* (2018.01); *G16H 10/65* (2018.01); *G16H 20/13* (2018.01); *G16H 40/63* (2018.01)

(58) Field of Classification Search
CPC ........ G16H 50/30; G16H 40/63; G16H 10/65; G16H 20/13
(Continued)

(56) References Cited

U.S. PATENT DOCUMENTS 8,807,131 B1     8/2014  Tunnell et al.
12,171,740 B2 *  12/2024  Azouz ................. A61K 31/711
(Continued)

FOREIGN PATENT DOCUMENTS

JP        2009-532072 A     9/2009
JP        2015-219617 A     12/2015
WO      WO 2016/172614 A1   10/2016

OTHER PUBLICATIONS

European Patent Office, Extended European Search Report and Opinion, EP Patent Application No. 18864689.7, Jun. 7, 2021, ten pages.
(Continued)

*Primary Examiner* — Michael I Ezewoko
*Assistant Examiner* — Rachael Sojin Stone
(74) *Attorney, Agent, or Firm* — McDermott Will & Schulte LLP

(57) ABSTRACT

This description provides asthma risk notifications in advance of predicted rescue usage events in order to help effect behavior changes in a patient to prevent those events from occurring. Rescue medication events, changes in environmental conditions, and other contextually relevant information are detected by sensors associated with the patient's medicament device/s and are collected from other sources, respectively, to provide a basis to determine a patient's risk score. This data is analyzed to determine the severity of the patient's risk for an asthma event and is used to send notifications accordingly.

13 Claims, 19 Drawing Sheets

(51) Int. Cl.
   *G16H 20/13*        (2018.01)
   *G16H 40/63*        (2018.01)
(58) Field of Classification Search
   USPC .......................................................... 705/2
   See application file for complete search history.

(56)                    References Cited

U.S. PATENT DOCUMENTS

| | | |
|---|---|---|
| 2003/0214409 A1 | 11/2003 | Hickle |
| 2008/0249983 A1 | 10/2008 | Meisels et al. |
| 2008/0300497 A1 | 12/2008 | Krause et al. |
| 2011/0184250 A1 | 7/2011 | Schmidt et al. |
| 2012/0010867 A1 | 1/2012 | Eder |
| 2012/0266251 A1 | 10/2012 | Birtwhistle et al. |
| 2013/0282295 A1 | 10/2013 | White et al. |
| 2014/0006314 A1 | 1/2014 | Yu et al. |
| 2014/0142456 A1 | 5/2014 | Fischer et al. |
| 2014/0334264 A1 | 11/2014 | Thaker |
| 2016/0314256 A1 | 10/2016 | Su et al. |
| 2017/0109493 A1* | 4/2017 | Hogg ..................... G16H 10/60 |
| 2017/0238850 A1 | 8/2017 | Gonzales et al. |
| 2018/0158552 A1 | 6/2018 | Liu et al. |
| 2019/0180379 A1 | 6/2019 | Nayak et al. |
| 2020/0058403 A1* | 2/2020 | Barrett ................... G16H 50/30 |
| 2020/0194125 A1* | 6/2020 | Adolphus ............. H04W 4/029 |
| 2022/0115107 A1* | 4/2022 | Gondalia ............... G16H 80/00 |
| 2022/0319660 A1* | 10/2022 | Belanger-Basset .... G06V 40/28 |
| 2022/0375623 A1* | 11/2022 | Hirons ................... G16H 50/70 |
| 2022/0405619 A1* | 12/2022 | Ramamurthy ...... G06F 16/9024 |
| 2024/0153608 A1* | 5/2024 | Ma ......................... G16H 10/60 |

OTHER PUBLICATIONS

Frey, U. et al., "Complexity of Chronic Asthma and Chronic Obstructive Pulmonary Disease: Implications for Risk Assessment, and Disease Progression and Control," The Lancet, vol. 372, No. 9643, Sep. 20, 2008, pp. 1088-1099.

PCT International Search Report and Written Opinion, PCT Application No. PCT/US2018/048909, Nov. 2, 2018, 13 pages.

Silkoff, P.E. et al., "The Aerocrine exhaled nitric oxide monitoring system NIOX is cleared by the US Food and Drug Administration for monitoring therapy in asthma," 2004, pp. 1241-1256.

United States Office Action, U.S. Appl. No. 15/724,968, filed Aug. 31, 2020, 14 pages.

United States Office Action, U.S. Appl. No. 15/724,968, filed Apr. 1, 2020, 25 pages.

United States Office Action, U.S. Appl. No. 15/724,968, filed Aug. 20, 2019, 16 pages.

Japan Patent Office, Office Action, Japanese Patent Application No. 2020-541336, Mar. 28, 2022, four pages.

\* cited by examiner

100

200

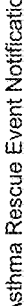

Asthma Rescue Event Notification

Client Device 110
Provider 112

Sensor
120

Client Device 110
Patient 111

Application Server
130

Initialize Asthma Profile
405

Detect Rescue Event
410

Store Event Info
415

Detect Triggering Condition
420

Access Contextual Data
425

Perform Asthma Risk
Analysis
430

Generate Risk Score
Notifications
435

Display Patient Results
440

Display Provider Results
445

Asthma Profile Data

Rescue Event Data

Rescue Event Data

Risk Index Notification

Risk Score Notification

Event Detection and Reporting
Initiated at Step 410

Training Data Set 650

| | Day | Month | Day of Week | Latitude | Longitude | Visibility | Temperature | Humidity | Wind Speed | Station Pressure | Wind Direction | $NO_2$ | $O_3$ | $SO_2$ | $PM2.5$ | $PM10$ | AQI | Disease Type | # Days on Propeller | Adherence | Cumulative Avg. Rescue Events |
|---|---|---|---|---|---|---|---|---|---|---|---|---|---|---|---|---|---|---|---|---|---|
| 1-7 | $x_1$ | $x_2$ | $x_3$ | $x_4$ | $x_5$ | $x_6$ | $x_7$ | $x_8$ | $x_9$ | $x_{10}$ | $x_{11}$ | $x_{12}$ | $x_{13}$ | $x_{14}$ | $x_{15}$ | $x_{16}$ | $x_{17}$ | $x_{18}$ | $x_{19}$ | $x_{20}$ |
| 8 | $x'_1$ | $x'_2$ | $x'_3$ | $x'_4$ | $x'_5$ | $x'_6$ | $x'_7$ | $x'_8$ | $x'_9$ | $x'_{10}$ | $x'_{11}$ | $x'_{12}$ | $x'_{13}$ | $x'_{14}$ | $x'_{15}$ | $x'_{16}$ | $x'_{17}$ | $x'_{18}$ | $x'_{19}$ | $x'_{20}$ |
| 9 | $x''_1$ | $x''_2$ | $x''_3$ | $x''_4$ | $x''_5$ | $x''_6$ | $x''_7$ | $x''_8$ | $x''_9$ | $x''_{10}$ | $x''_{11}$ | $x''_{12}$ | $x''_{13}$ | $x''_{14}$ | $x''_{15}$ | $x''_{16}$ | $x''_{17}$ | $x''_{18}$ | $x''_{19}$ | $x''_{20}$ |
| 10 | $x'''_1$ | $x'''_2$ | $x'''_3$ | $x'''_4$ | $x'''_5$ | $x'''_6$ | $x'''_7$ | $x'''_8$ | $x'''_9$ | $x'''_{10}$ | $x'''_{11}$ | $x'''_{12}$ | $x'''_{13}$ | $x'''_{14}$ | $x'''_{15}$ | $x'''_{16}$ | $x'''_{17}$ | $x'''_{18}$ | $x'''_{19}$ | $x'''_{20}$ |
| 11 | $x''''_1$ | $x''''_2$ | $x''''_3$ | $x''''_4$ | $x''''_5$ | $x''''_6$ | $x''''_7$ | $x''''_8$ | $x''''_9$ | $x''''_{10}$ | $x''''_{11}$ | $x''''_{12}$ | $x''''_{13}$ | $x''''_{14}$ | $x''''_{15}$ | $x''''_{16}$ | $x''''_{17}$ | $x''''_{18}$ | $x''''_{19}$ | $x''''_{20}$ |

Parameters

A

Label

| Risk Classification (High/Low) |
|---|
| 0 |
| 1 |
| 1 |
| 0 |
| 1 |

C

Machine Learning Model

B

FIG. 6C 7-day sum
= 30 events
2 events
Is current day total (2 events)
GREATER than 5% of 7-day
sum (30 events)?
(0.05) (30) = 1.5
2 > 1.5? <u>YES!</u>
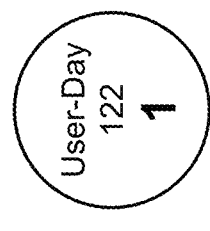
User-Day
122
1
7-day sum
= 30 events
1 event
Is current day total (1 event)
GREATER than 5% of 7-day
sum (30 events)?
(0.05) (30) = 1.5
1 > 1.5? <u>NO!</u>
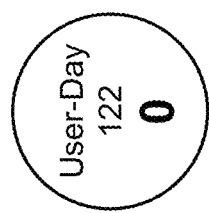
User-Day
122
0
*FIG. 6D*

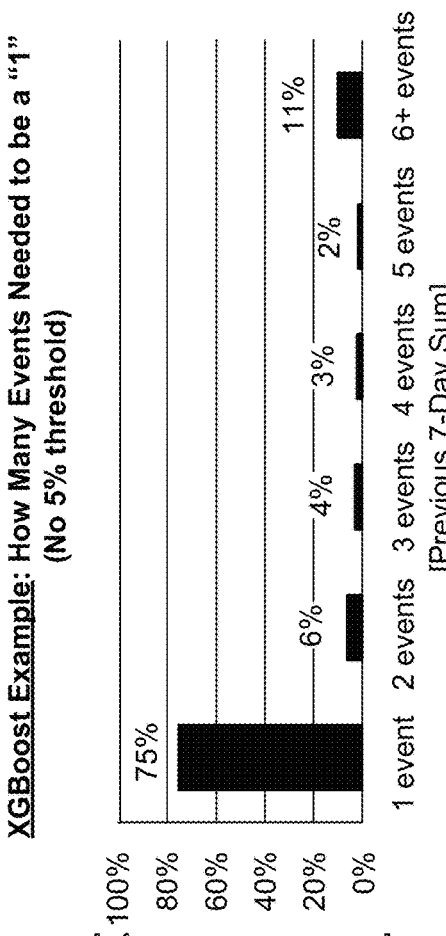
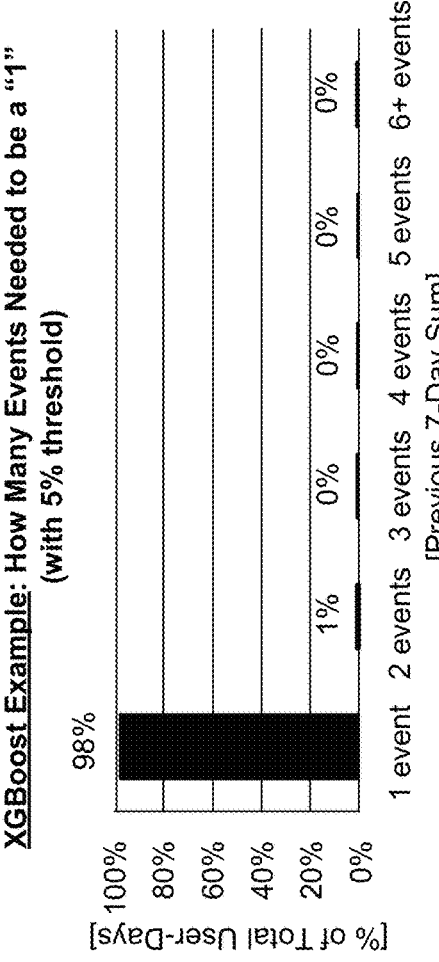
\* Data source: model predictions on 20% sample of new database, n = 35,848 (user-days)
*FIG. 7A*

Results from V1 Model

| | >20% | >30% | >40% | >50% | >60% | >70% |
|---|---|---|---|---|---|---|
| % "1s" | 26% | 26% | 25% | 23% | 22% | 20% |
| AUC Score | 0.97 | 0.97 | 0.97 | 0.963 | 0.940 | 0.939 |
| Accuracy | 0.91 | 0.91 | 0.91 | 0.89 | 0.87 | 0.85 |
| Sensitivity (NPV) | 0.90 | 0.90 | 0.90 | 0.90 | 0.91 | 0.90 |
| Specificity (PPV) | 0.91 | 0.91 | 0.91 | 0.89 | 0.85 | 0.84 |

*FIG. 7B*

| XGBoost Example: Model Outputs | |
| --- | --- |
| AUC Score | 0.88 |
| Accuracy | 0.81 |
| Sensitivity (NPV) | 0.81 |
| Specificity | 0.80 |

*FIG. 7C*

XGBoost Example: Low, Med, High Risk Distribution

54%

38%

7%

Low Risk    Medium Risk    High Risk

60%
50%
40%
30%
20%
10%
0%

* Data source: model predictions on 20% new dataset, n = 35,848 (user-days)

XG Boost Example: Risk Predictions by Daily Rescue Event Totals

100%
80%
60%
40%
20%
0%

Low Risk        Medium Risk        High Risk

☐ 0    ☒ 1-3    ☒ 3-6    ▥ 6-10    ■ 10+

* Data source: Model predictions on test set (random sample of 20% of total file), n = 35,848

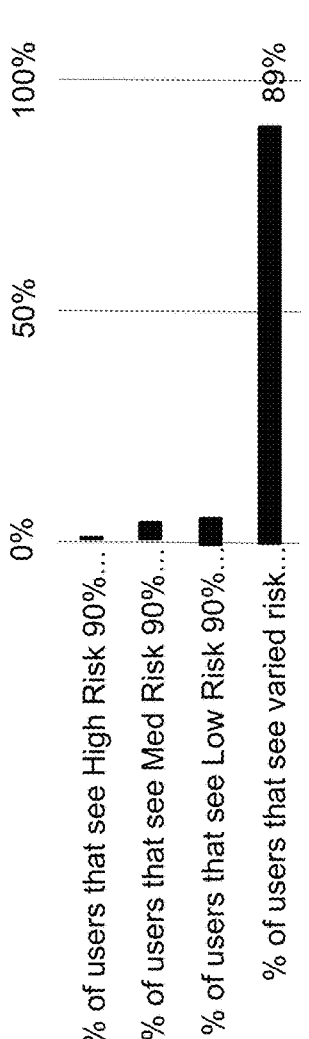

XG Boost Example: Risk Score Variance Across Users With 5+ Days of Data

% of users that see High Risk 90%...

% of users that see Med Risk 90%...

% of users that see Low Risk 90%...

% of users that see varied risk... — 89%

0%    50%    100%

*Data source: model predictions on 20% sample of new dataset, n = 3,982 (users)*

Demographics Breakdown

| | High 90% of Time | Med 90% of Time | Low 90% of Time |
|---|---|---|---|
| Average daily rescue puffs | 5.62 | 0.98 | 0.06 |
| Percent COPD* | 83% | 14% | 5% |

*Patients with COPD in new test ~10%*

*FIG. 7G*

XGBoost Example Model: Percent "High Risk" by Normalized Day: First 7 Days

*FIG. 7I*

PRE-EMPTIVE ASTHMA RISK NOTIFICATIONS BASED ON MEDICAMENT DEVICE MONITORING

CROSS REFERENCE TO RELATED APPLICATION

This application is a continuation of U.S. patent application Ser. No. 15/724,968, filed on Oct. 4, 2017, which is herein incorporated by reference in its entirety for all purposes.

BACKGROUND

Field of Art

The disclosure relates generally to methods of improving treatment for patients who use inhalers, and more specifically to determining a patient's risk of asthma-related rescue events.

Description of the Related Art

Asthma remains a significant and costly public health problem. Worldwide, the World Health Organization estimates the population with asthma may be 300 million, and predicts that it will rise to 400 million by 2025. In the United States, asthma affects 1 in 12 individuals in the U.S. and prevalence is on the rise, leading to more than $56 billion per year in health care utilization costs.

Despite the development of new medications, rates of hospitalizations and emergency room visits have not declined. Each year in the United States the disease causes approximately 2 million emergency department visits, 500, 000 hospitalizations, and 5,000 deaths. In addition, asthma is responsible for an estimated 15 million missed days of school, and 12 million days of work. Total annual costs to US health insurers and employers are greater than $18 billion.

The majority of these exacerbations could be prevented with currently available treatments, however, only 1 in 5 asthmatics has the disease under control. Newly revised national guidelines urge doctors to more closely monitor whether treatment is controlling everyday symptoms and improving quality of life. Physicians, however, have few available tools to assess how well their patients are doing day-to-day. An increasing number of physicians have begun to use periodic, written questionnaires (such as the Asthma Control Test) to monitor patients and determine their level of control. These instruments require patients to accurately recall and report the frequency of symptoms, inhaler usage, and activity level and restriction over some period of time (usually two to four weeks). As a result, these questionnaires are subject to error introduced by biases (recall), different interpretations of symptoms, and behaviors (non-adherence), and only provide information at the time they are used More generally, medicament devices such as inhalers allow patients to manage respiratory symptoms such as constricted airflow. Many respiratory disease patients, such as sufferers of asthma, COPD, and cystic fibrosis, have symptoms that are related to environmental triggers and factors such as air quality, weather, land use, and the like. A patient being aware of which environmental triggers and factors affect their symptoms allows the patient to better manage their symptoms and reduce the chances for needing emergency medical care. However, a particular patient or group of patients may have sensitivities to multiple triggers and factors. Knowing which of dozens, hundreds, or more triggers and factors a patient is sensitive to and monitoring those triggers and factors for use in managing symptoms is a complex task and not currently feasible for many patients and providers.

SUMMARY

An asthma analytics system is a unified platform for treating, monitoring, and managing rescue events resulting from asthma. The asthma analytics system tracks asthma rescue medication events by receiving event notifications from a sensor attached to a medicament device (e.g., inhaler) used by a patient who has authorized the asthma analytics system to help manage their asthma. The sensor, when attached to or incorporated in a metered dose inhaler or other medicament device, records the geographical location, time, and date of the rescue usage event, and communicates that information to the asthma analytics system. The asthma analytics system analyzes the received events (both the most recent and previously received events) in real time or near-real time, and delivers a risk assessment and information to guide and manage the disease in the form of a notification to patients and the healthcare providers.

The risk score is determined using a combination of parameters including a patient's medical history, a patient's current situation on a day-to-day basis, and environmental conditions relating to atmospheric and weather conditions. The relationship between these parameters and risk assessment generated for the patient is embodied in a machine learned model. The model, and system more generally, is capable of receiving input values for the parameters and categorizing a patient's risk score to provide a risk assessment with accurate and medically relevant treatment options to mitigate the risk.

By ingesting information about the timing, frequency, and location of the usage of the medication along with other contextually relevant parameter information, the asthma analytics system helps prevent the occurrence of future asthma rescue usage events by suggesting immediately applicable changes in behavior or environment in advance of those predicted events. This facilitates better management of an asthma treatment by the patient and their health care provider, and improve recognition of specific locations that precipitate rescue events so that the patient may avoid or accommodate these locations in the future.

According to an embodiment, a method for determining a patient's risk of asthma-related rescue events includes accessing a set of historical rescue inhaler usage events for a patient. The set of events are previously received from a client device or attachment associated with a rescue inhaler unit or from the rescue inhaler unit that provided a rescue medication to the patient as part of each event. The method also includes determining a patient-specific baseline risk threshold based on the set of events. In response to a triggering condition, the method includes accessing a set of parameter values for a model predicting asthma risk and accessing a set of input values. Also in response to a triggering condition, the method includes inputting the parameter values, input values, and a baseline risk threshold into a function to determine the risk score. In response to a triggering condition, the method includes sending a notification with details of the risk score to the device.

In one or more embodiments, the method also includes receiving a history of rescue inhaler usage events from a client device, attachment, or rescue inhaler unit.

In one or more embodiments, the threshold is determined with respect to a prior period which includes events from a window of time preceding the current time.

In one or more embodiments, the threshold is determined as a percentage of a sum of the events within the prior period.

In one or more embodiments, the threshold is periodically determined.

In one or more embodiments, the triggering condition includes a threshold change in a physical location of the client device.

In one or more embodiments, the triggering condition includes a periodic conclusion of a time interval.

In one or more embodiments, the triggering condition includes a threshold change in the input value of at least one of a plurality of parameters.

In one or more embodiments, the triggering condition includes an occurrence of a current rescue inhaler usage event, received from the client device, attachment, or rescue inhaler that provided the rescue medication to the patient as part of the current event.

In one or more embodiments, the parameter values are determined using a boosted gradient model.

In one or more embodiments, the risk score is a numerical value representing a likelihood that the patient will exceed the threshold that day.

In one or more embodiments, the parameters include at least one event data parameter and at least one contextual data parameter.

In one or more embodiments, the parameters include one or more of the following: at least one historical patient parameter, further comprising a cumulative patient history of rescue events, a patient history of events occurring at night, a cumulative count of the days using a rescue unit, a disease type, and an adherence record.

In one or more embodiments, the parameters include one or more of the following: at least one current patient parameter, further comprising a current latitude and longitude coordinate of the client device, a current location, a current date, and a difference in number of rescue puffs taken and prescribed for the rescue event.

In one or more embodiments, the parameters include one or more of the following: at least one air pollutant parameter, further comprising: ozone molecules, nitrogen dioxide molecules, sulfur dioxide molecules, particulate matter, 2.5 micrometers or less, particulate matter, 1 micrometer or less, and the air quality index.

In one or more embodiments, the parameters include one or more of the following: at least one weather parameter, further comprising: temperature, humidity, wind speed, wind direction, station pressure, and visibility.

In one or more embodiments, the parameters include one or more of the following: temperature, relative humidity, wind speed parameter, nitrogen dioxide ($NO_2$); sulfur dioxide ($SO_2$); particular matter 2.5 micrometers or less ($PM_{2.5}$); and particulate matter 1 micrometers or less ($PM_{1.0}$).

In one or more embodiments, the parameters include a number of days where rescue inhaler usage events are monitored by a computing system external to the rescue inhaler unit.

In one or more embodiments, the function determines whether the number of rescue inhaler usage events for a given day exceeds the threshold.

In one or more embodiments, the risk notification is presented at a first time that is different from a second time when the risk threshold is determined.

In one or more embodiments, the risk notification comprises information content regarding the triggering condition.

In one or more embodiments, the risk notification comprises informational content regarding at least one of the following: the events, the baseline risk threshold, and a risk categorization based on the risk score.

In one or more embodiments, the risk notification further comprises informational content regarding the rescue event, wherein the informational content further comprises a subset of parameters responsible for a change in risk categorization compared to a previous time period.

In one or more embodiments, the risk notification further comprises informational content regarding the rescue event, wherein the informational content further comprises a recommendation regarding how to prevent further rescue inhaler events wherein the recommendation is based on the subset of parameters responsible for the change in risk categorization.

BRIEF DESCRIPTION OF DRAWINGS

FIG. 4 is an interaction diagram for providing asthma risk-based notifications based on medicament device monitoring, according to one embodiment.

FIG. 6C is a diagram illustrating the method for training the model using the training data set, according to one embodiment.

FIG. 6D is a diagram illustrating the method of establishing the threshold for risk identification, according to one embodiment.

FIGS. 7A-7I are diagrams characterizing and analyzing the data used for testing the asthma risk analysis, according to one embodiment.

The figures depict various embodiments of the presented invention for purposes of illustration only. One skilled in the art will readily recognize from the following discussion that alternative embodiments of the structures and methods illustrated herein may be employed without departing from the principles described herein.

DETAILED DESCRIPTION

I. System Environment

Figure 1:
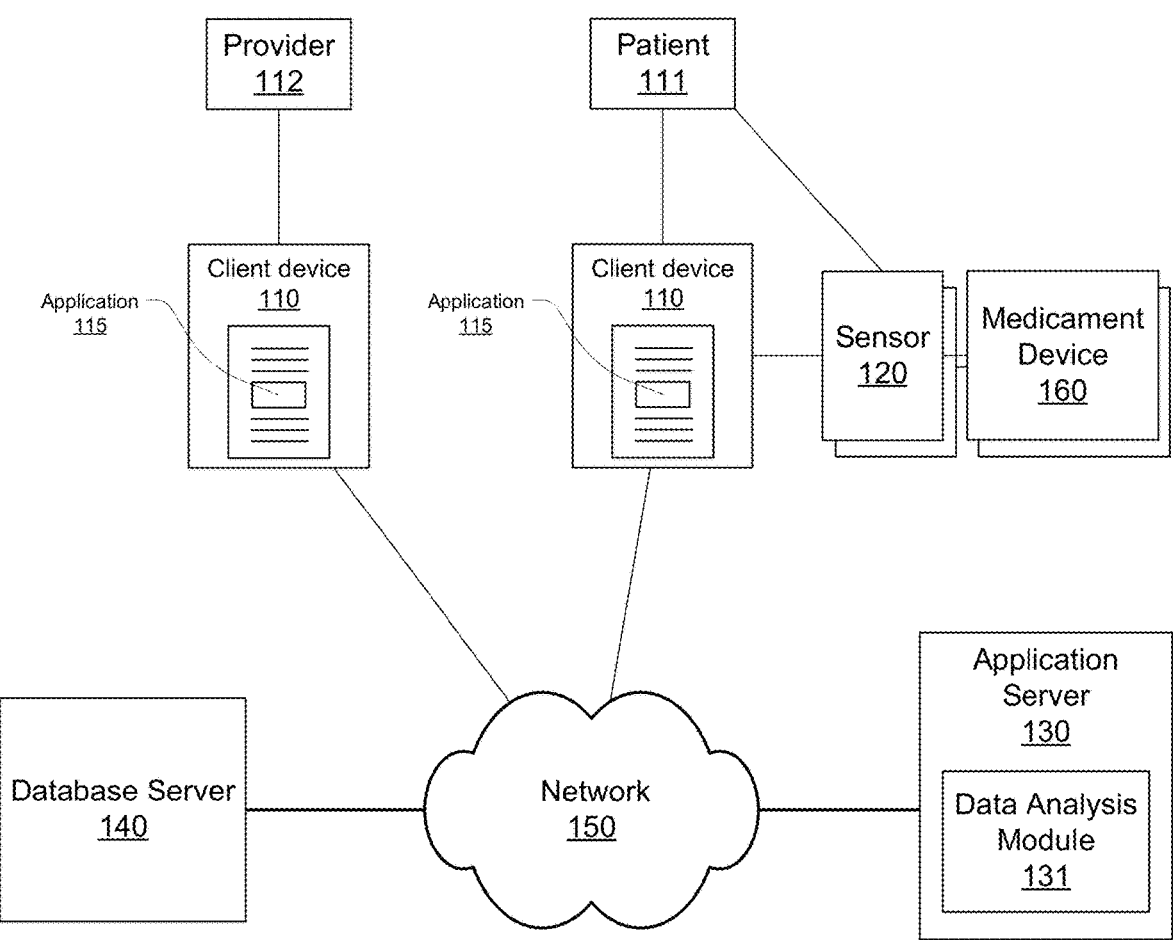
FIG. 1 shows an asthma analytics system for monitoring accurate, real-time medicament device usage, performing analytics on that data, and providing asthma rescue event risk notifications, according to one embodiment.

FIG. 1 shows an asthma analytics system 100 for monitoring accurate, real-time medicament device events, performing analytics on that data, and providing asthma rescue event risk notifications, according to one embodiment.

The asthma analytics system includes client computing devices 110, a medicament device sensor 120, a medicament device 160, an application server 130, database server 140, and a network 150. Although FIG. 1 illustrates only a single instance of most of the components of the asthma analytics system 100, in practice more than one of each component may be present, and additional or fewer components may be used.

I.A. Client Device and Application

The client devices 110, at the behest of their users, interact with the asthma analytics system 100 via the network 150. For purposes of explanation and clarity it is useful to identify at least two different types of users. A patient 111 is a user burdened with asthma who makes use of the asthma analytics system 100 at least in part to obtain personalized asthma rescue event risk notifications provided by the server 130 and asthma management notifications created by their health care provider 112. Such notifications can be provided in exchange for the user's permission to allow the asthma analytics system 100 to monitor the patient's 111 medicament device 160 usage. As will be explained below, medication events are detected by a sensor 120 associated with the medicament device 160 and the user's client device 100, which in turn reports to the application server 130, which in turn can initiate a process to generate risk notifications which are provided to the user through the client device 110.

Another type of user is a healthcare provider 112 who, again with the patient's 111 express permission, also receives notifications regarding a patient's asthma management, as well as aggregated asthma community rescue event data and derived statistics regarding asthma events and other associated data. Other types of users are also contemplated, such as parents/guardians of patients 111 who may also want to receive notifications in the event that their own client devices 110 are distinct from that of their children.

The client device 110 is a computer system. An example physical implementation is described more completely below with respect to FIG. 2. The client device 110 is configured to wirelessly communicate with the asthma analytics system 100 via network 150. With network 150 access, the client device 110 transmits to system 100 the user's geographical location and the time of a rescue medication event, as well as information describing the event as received from the associated medicament device sensor 120 (referred to throughout as "sensor 120").

Regarding user location and event times, the client device 110 may determine the geographical location and time of a rescue event through use of information about the cellular or wireless network 150 to which it is connected. For example, the current geographical location of the client device 110 may be determined by directly querying the software stack providing the network 150 connection. Alternatively, the geographical location information may be obtained by pinging an external web service (not shown in FIG. 1) made accessible via network 150. The time of an event can be provided by the sensor 120 as part of the event data or added to event data by querying an appropriate software routine available as part of the client device's native operating system.

In addition to communicating with the application server 130, client devices 110 connected wirelessly to the asthma analytics system 100 may also exchange information with other connected client devices 110. For example, through a client software application 115, a healthcare provider 112 may receive a risk exacerbation notification describing a recent rescue event about a patient 111, then in response send a recommendation to the patient 111 for post-asthma rescue event treatment. Similarly, through application 115 patients 111 may communicate with their health care providers 112 and other patients 111.

Application 115 provides a user interface (herein referred to as a "dashboard") that is displayed on a screen of the client device 110 and allows a user to input commands to control the operation of the application 115. The dashboard is the mechanism by which healthcare providers 112 and patients 111 access the COPD analytics system 100. For example, the dashboard allows patients 111 and providers 112 to interact with each other, receive asthma rescue event risk notifications, exchange messages about treatment, provide and receive additional event and non-event data, and so on. Application 115 may be coded as a web page, series of web pages, or content otherwise coded to render within an internet browser. Application 115 may also be coded as a proprietary application configured to operate on the native operating system of the client device 110. The dashboard is more completely described below in conjunction with FIG. 3.

In addition to providing the dashboard, application 115 may also perform some data processing on asthma rescue event data locally using the resources of client device 110 before sending the processed data through the network 150. Event data sent through the network 110 is received by the application server 130 where it is analyzed and processed for storage and retrieval in conjunction with database server 140. The application server 130 may direct retrieval and storage request to the database system 130 as required by the client application 115.

The client device 110 communicates with the sensor 120 using a network adapter and either a wired or wireless communication protocol, an example of which is the Bluetooth Low Energy (BTLE) protocol. BTLE is a short-ranged, low-powered, protocol standard that transmits data wirelessly over radio links in short range wireless networks. After the sensor 120 and client device 110 have been paired with each other using a BTLE passkey, the sensor 120 automatically synchronizes and communicate information relating to medicament device usage with the client device 110. If the sensor 120 hasn't been paired with a client device 110 prior to a rescue medication event, the information is stored locally until such a pairing occurs. Upon pairing, the sensor 120 communicates any stored event records to the client device 110. In other implementations, other types of wireless connections are used (e.g., infrared or 802.11).

Although client devices 110 and medicament devices 160 are described above as being separate physical devices (such as smart phones and inhalers, respectively), in the future it is contemplated the medicament devices 160 may include not only sensors 120 integrated into a single housing with the device 160, but also aspects of the client device 110. For example, a medicament device 160 may include an audio-visual interface including a display or other lighting elements as well as speakers for presenting visual audible information. In such an implementation the medicament device 160 itself may present the contents of notifications provided by the server 130 directly, in place of or in addition to presenting them through the client devices 110.

I.B. Medicament Device and Sensor

The medicament device 160 is a medical device used to deliver medication to the lungs of a user experiencing constricted respiratory airflow. Medicament devices (e.g. inhalers) are typically portable and small enough to be carried by hand for ease of accessibility when treating respiratory attacks. In one embodiment, medicine is delivered in aerosol form through a medicament device 160 such as a metered dose inhaler. Metered dose inhalers included a pressured propellant canister of aerosol medicine, a metering valve for delivering a regulated medicine dosage amount, and a plastic holder that holds the pressurized canister and also forms a mouthpiece for delivery of the medicine. In another embodiment, medicine is delivered in dry powder form through a medicament device 160 such as a dry powder inhaler. Dry powder inhalers may have Cartesian ovular shaped bodies that house wheel and gear mechanisms enabling a user to index through a strip of dry powder medication. The bodies of dry powder inhalers also include a manifold and a mouthpiece to deliver dry powder to the user. Examples of controller medications that are dispensed by a controller medicament device 160 include beclomethasone, budesonide, and fluticasone as well as combinations of those medications with a long-acting bronchodilator such as salmeterol or formoterol. Examples of rescue medications that are dispensed by a rescue medicament device 160 include albuterol, salbutamol, levalbuterol, metaproterenol, and terbutaline.

Each patient may be associated with more than one medicament device 160. For example, the patient may have a rescue medicament device 160 that dispenses rescue medication, and a controller medicament device 160 that dispenses controller medication. Similarly, each patient may be associated with more than one sensor 120, each chosen to operate with one of the patient's medicament devices 160.

Generally, a sensor 120 is a physical device that monitors the usage of the medicament dispenser 160. The sensor 120 is either removably attachable to the medicament dispenser without impeding the operation of the medication dispenser, or the sensor 120 is an integrated component that is a native part of the medicament dispenser 160 as made available by its manufacturer.

The sensor 120 includes its own network adapter (not shown) that communicates with the client device 110 either through a wired connection, or more typically through a wireless radio frequency connection. In one embodiment, the network adapter is a Bluetooth Low Energy (BTLE) wireless transmitter, however in other embodiments other types of wireless communication may be used (e.g., infrared, 802.11).

The sensor 120 may also be configured to communicate more directly with the application server 130. For example, if the network adapter of the sensor 120 is configured to communicate via a wireless standard such as 802.11 or LTE, the adapter may exchange data with a wireless access point such as a wireless router, which may in turn communicate with the application server 130 without necessarily involving the client device 110 in every exchange of data. These two methods of communicating are not mutually exclusive, and the sensor 120 may be configured to communicate with both the client device 110 and the application server 130, for example using redundant transmission to ensure event data arrives at the application server 130 or to provide information directly to the client device 110 while the application server 130 is determining what notification to provide in response to an event.

As introduced above, the sensor 120 captures data about usage of the medicament device 160. Specifically, each sensor 120 captures the time and geographical location of the rescue medication event, that is, usages of the rescue medicament device 160, by the patient 111. Each sensor 120 transmits the event data in real-time or as soon as a network connection is achieved, automatically without input from the patient 111 or health care provider 112. The medication event information is sent to the application server 130 for use in analysis, generation of asthma rescue event notifications, and in aggregate analyses of event data across multiple patients.

To accomplish this goal, there are a number of different ways for the sensor 120 to be constructed, and in part the construction will depend upon the construction of the medicament device itself 160. Generally, all sensors 120 will include an onboard processor, persistent memory, and the network adapter mentioned above that together function to record, store, and report medication event information to the client device 110 and/or server 130. Sensors 120 may also include a clock for recording the time and date of events.

Regarding specific sensor 120 constructions, traditional inhalers, such as mechanical dose counters, are not designed with sensors 120 in mind, and thus the sensor 120 may be constructed accordingly. Some implementations in this manner include mechanical, electrical, or optical sensors to detect movement of the device 160, priming of the device, activation of the device, inhalation by the user, etc. In contrast, modern inhalers, such as deflectable membrane dose counters, include electrical circuitry may report event information as an electrical data signal which a sensor 120 is designed to receive and interpret, for example the medicament device 160 itself may report movement, priming, and activation to the sensor 120.

More information regarding hardware and software components for the sensors 120 and medicament devices 160, as well as the interaction between them to record rescue medication events can be found in U.S. patent application Ser. No. 12/348,424, filed Jan. 1, 2009, and International Application No. PCT/US2014/039014, filed May 21, 2014, both of which are incorporated by reference herein in their entirety.

I.C. Application Server

Figure 2:
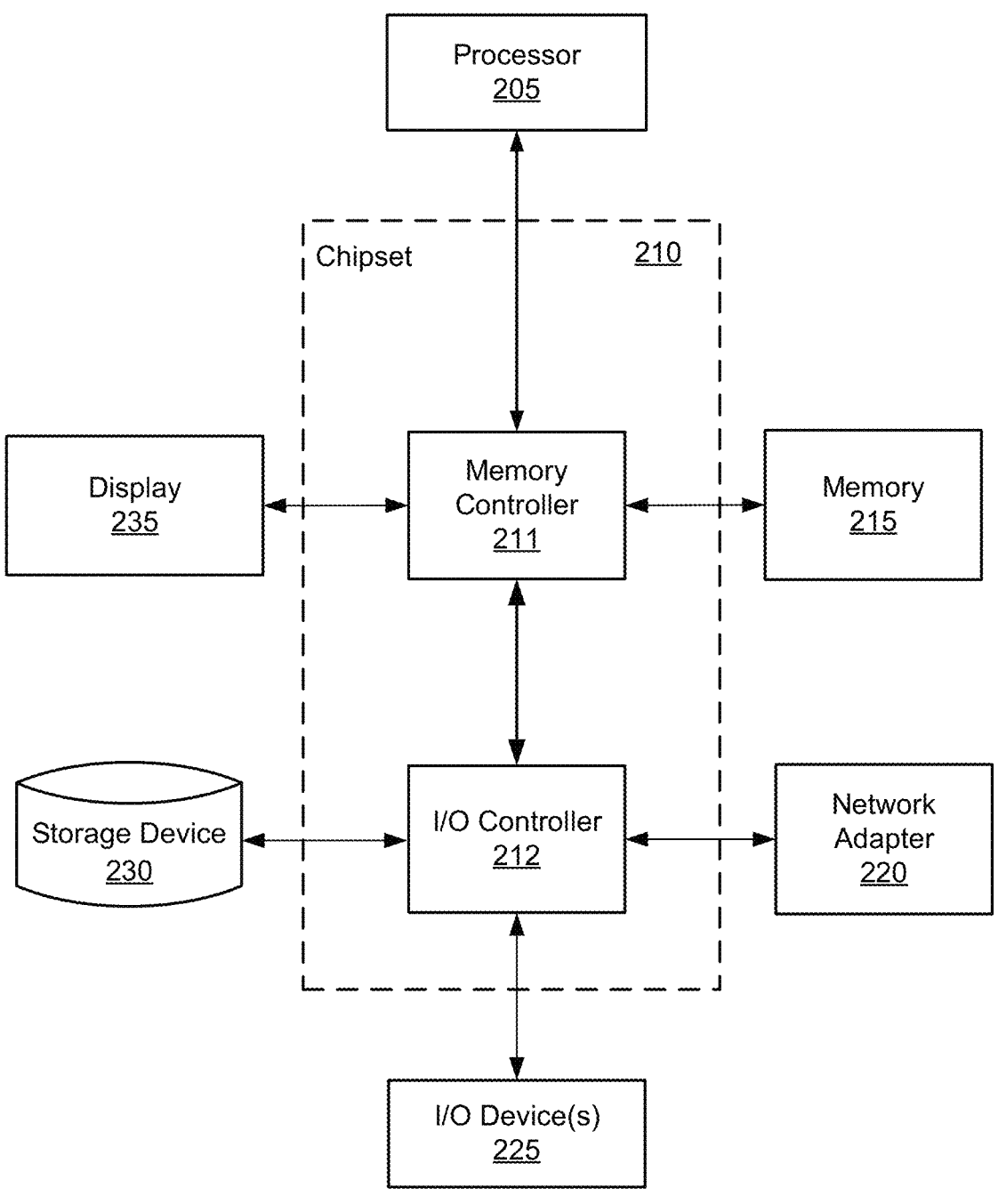
FIG. 2 is a high-level block diagram illustrating an example of a computing device used in either as a client device, application server, and/or database server, according to one embodiment.

The application server 130 is a computer or network of computers. Although a simplified example is illustrated in FIG. 2, typically the application server will be a server class system that uses powerful processors, large memory, and faster network components compared to a typical computing system used, for example, as a client device 110. The server typically has large secondary storage, for example, using a RAID (redundant array of independent disks) array and/or by establishing a relationship with an independent content delivery network (CDN) contracted to store, exchange and transmit data such as the asthma notifications contemplated above. Additionally, the computing system includes an operating system, for example, a UNIX operating system, LINUX operating system, or a WINDOWS operating system. The operating system manages the hardware and software resources of the application server 130 and also provides various services, for example, process management, input/output of data, management of peripheral devices, and so on. The operating system provides various functions for managing files stored on a device, for example, creating a new file, moving or copying files, transferring files to a remote system, and so on.

The application server 130 includes a software architecture for supporting access and use asthma analytics system 100 by many different client devices 110 through network 150, and thus at a high level can be generally characterized as a cloud-based system. The application server 130 generally provides a platform for patients 111 and healthcare providers 112 to report data recorded by the sensors associated with their medicament devices 160 including both rescue medication and controller medication events, collaborate on asthma treatment plans, browse and obtain information relating to their condition and geographic location, and make use of a variety of other functions.

Generally, the application server 130 is designed to handle a wide variety of data. The application server 130 includes logical routines that perform a variety of functions including checking the validity of the incoming data, parsing and formatting the data if necessary, passing the processed data to a database server 140 for storage, and confirming that the database server 140 has been updated.

The application server 130 stores and manages data at least in part on a patient by patient basis. Towards this end, the application server 130 creates a patient profile for each user. The patient profile is a set of data that characterizes a patient 111 of the asthma analytics system 100. The patient profile may include identify information about the patient such as age, gender, current rescue medication, current controller medication, notification preferences, a controller medication adherence plan, a patients relevant medical history, and a list of non-patient users authorized to access to the patient profile. The profile may further specify a device identifier, such as a unique media access control (MAC) address identifying the one or more client devices 110 or sensors 120 authorized to submit data (such as controller and rescue medication events) for the patient.

The profile may specify which different types of notifications are provided to patients 111 and their personal healthcare providers 112, as well as the frequency with which notifications are provided. For example, a patient 111 may authorize a healthcare provider 112 to receive notifications indicating a rescue event. The patient 111 may also authorize their healthcare provider 112 be given access to their patient profile and rescue event history. If the healthcare provider 112 is provided access to the patient profile of the patient 111, the healthcare provider may specify controller adherence or rescue medication plans. Medication plans may include a prescribed number of doses per day for controller medications.

The application server 130 also creates profiles for health care providers 112. A health care provider profile may include identifying information about the health care provider 112, such as the office location, qualifications and certifications, and so on. The health care provider profile also includes information about their patient population. The provider profile may include access to all of the profiles of that provider's patients, as well as derived data from those profiles such as aggregate demographic information, rescue and controller medication event patterns, and so on. This data may be further subdivided according to any type of data stored in the patient profiles, such as by geographic area (e.g., neighborhood, city) over by time period (e.g., weekly, monthly, yearly).

The application server 130 receives rescue medication event information from the client device 110 or the sensor 120, triggering a variety of routines on the application server 130. In the example implementations described below, the data analysis module 131 executes routines to access asthma event data as well as other data including a patient's profile, analyze the data, and output the results of its analysis to both patients 111 and providers 112. This process is generally referred to as an asthma risk analysis. The asthma risk analysis may be performed at any point in time, in response to a rescue event, due to a relevant change in the patient's environment, and in response to any one of a number of triggering conditions discussed further below.

Other analyses are also possible. For example, a risk analysis may be performed on rescue and controller medication use for multiple patients to identify based on spatial/temporal clusters (or outbreaks) of medication use based on historically significant permutations from individual, geographic, clinical, epidemiologic, demographic, or spatial or temporal baselines or predicted or expected values. Other types of analyses may include daily/weekly adherence trends, adherence changes over time, adherence comparisons to other relevant populations (e.g., all patients, patients on a particular rescue medication or controller medication or combination thereof, identification of triggers (spatial, temporal, environmental), rescue use trends over time, and rescue use comparisons to other relevant populations.

Responsive to any analyses performed, the application server 130 prepares and delivers push notifications to send to patients 111, authorized healthcare providers 112, and/or other users provided access to the patient's profile. Notifications can provide details about the timing, location, and affected patient(s) 111 involved in a medication rescue event. Notifications may additionally comprise a distress or emergency signal that requests emergency assistance that are distributed to emergency assistance providers 112. Notifications may also include the results of the asthma risk analysis performed by the data analysis module 131. More information regarding the types of notifications that may be sent and the content they may contain is further described below.

In addition to providing push notifications in response to an asthma risk analysis, notifications may also be provided as pull notifications, at particular time intervals. Additionally, some notifications (whether push or pull) may be triggered not in response to an asthma risk analysis performed in response to a rescue medication event, but instead in response to a risk analysis performed in response to one of the underlying factors in the asthma risk analysis changing, such that an updated notification is warranted. For example, if weather conditions indicate that an increase in air pollution is occurring or is imminent, this may trigger the carrying out of asthma risk analyses for all patients located in the particular geographic area where the pollution is occurring.

Notifications are provided through the network 150 to client applications 115 in a data format specifically designed for use with the client applications, and additionally or alternatively may be provided as short message service (SMS) messages, emails, phone calls, or in other data formats communicated using other communication mediums.

I.D. Database Server

The database server 140 stores patient and provider data related data such as profiles, medication events, patient medical history (e.g., electronic medical records). Patient and provider data is encrypted for security and is at least password protected and otherwise secured to meet all Health Insurance Portability and Accountability Act (HIPAA) requirements. Any analyses (e.g., asthma risk analyses) that incorporate data from multiple patients (e.g., aggregate rescue medication event data) and are provided to users is de-identified so that personally identifying information is removed to protect patient privacy.

The database server 140 also stores non-patient data used in asthma risk analyses. This data includes regional data about a number of geographic regions such as public spaces in residential or commercial zones where patients are physically located and may be exposed to pollutants. This data may specifically include or be processed to obtain a patient's proximity to green space (areas including concentrated numbers of trees and plants). One example of regional data includes georeferenced weather data, such as temperature, wind patterns, humidity, the air quality index, and so on. Another example is georeferenced pollution data, including particulate counts for various pollutants at an instance of time or measured empirically. The regional data includes information about the current weather conditions for the time and place of the rescue event such as temperature, humidity, air quality index. All of the items of data above may vary over time, and as such the data itself may be indexed by time, for example separate data points may be available by time of day (including by minute or hour), or over longer periods such as by day, week, month, or season. Although the database server 140 is illustrated in FIG. 1 as being an entity separate from the application server 130 the database server 140 may alternatively be a hardware component that is part of another server such as server 130, such that the database server 140 is implemented as one or more persistent storage devices, with the software application layer for interfacing with the stored data in the database is a part of that other server 130.

The database server 140 stores data according to defined database schemas. Typically, data storage schemas across different data sources vary significantly even when storing the same type of data including cloud application event logs and log metrics, due to implementation differences in the underlying database structure. The database server 140 may also store different types of data such as structured data, unstructured data, or semi-structured data. Data in the database server 140 may be associated with users, groups of users, and/or entities. The database server 140 provides support for database queries in a query language (e.g., SQL for relational databases, JSON NoSQL databases, etc.) for specifying instructions to manage database objects represented by the database server 140, read information from the database server 140, or write to the database server 140.

With respect to the description of FIGS. 6A-6D below, the contents of the databases described with respect to those figures may be stored in databases physically proximate to the application server 130 and separate from database server 140 as illustrated. Alternatively, those databases may be a part of database server 140, in contrast to the description of FIGS. 6A-6D illustrating them as being within data analysis module 131. This and other variations thereupon are within the scope of this description.

I.E. Network

The network 150 represents the various wired and wireless communication pathways between the client 110 devices, the sensor 120, the application server 130, and the database server 140. Network 150 uses standard Internet communications technologies and/or protocols. Thus, the network 150 can include links using technologies such as Ethernet, IEEE 802.11, integrated services digital network (ISDN), asynchronous transfer mode (ATM), etc. Similarly, the networking protocols used on the network 150 can include the transmission control protocol/Internet protocol (TCP/IP), the hypertext transport protocol (HTTP), the simple mail transfer protocol (SMTP), the file transfer protocol (FTP), etc. The data exchanged over the network 150 can be represented using technologies and/or formats including the hypertext markup language (HTML), the extensible markup language (XML), etc. In addition, all or some links can be encrypted using conventional encryption technologies such as the secure sockets layer (SSL), Secure HTTP (HTTPS) and/or virtual private networks (VPNs). In another embodiment, the entities can use custom and/or dedicated data communications technologies instead of, or in addition to, the ones described above.

II. Example Computing Devices

FIG. 2 is a high-level block diagram illustrating physical components of an example computer 200 that may be used as part of a client device 110, application server 130, and/or database server 140 from FIG. 1, according to one embodiment. Illustrated is a chipset 210 coupled to at least one processor 205. Coupled to the chipset 210 is volatile memory 215, a network adapter 220, an input/output (I/O) device(s) 225, a storage device 230 representing a nonvolatile memory, and a display 235. In one embodiment, the functionality of the chipset 210 is provided by a memory controller 211 and an I/O controller 212. In another embodiment, the memory 215 is coupled directly to the processor 205 instead of the chipset 210. In some embodiments, memory 215 includes high-speed random access memory (RAM), such as DRAM, SRAM, DDR RAM or other random access solid state memory devices.

The storage device 230 is any non-transitory computer-readable storage medium, such as a hard drive, compact disk read-only memory (CD-ROM), DVD, or a solid-state memory device. The memory 215 holds instructions and data used by the processor 205. The I/O device 225 may be a touch input surface (capacitive or otherwise), a mouse, track ball, or other type of pointing device, a keyboard, or another form of input device. The display 235 displays images and other information from for the computer 200. The network adapter 220 couples the computer 200 to the network 150.

As is known in the art, a computer 200 can have different and/or other components than those shown in FIG. 2. In addition, the computer 200 can lack certain illustrated components. In one embodiment, a computer 200 acting as server 140 may lack a dedicated I/O device 225, and/or display 218. Moreover, the storage device 230 can be local and/or remote from the computer 200 (such as embodied within a storage area network (SAN)), and, in one embodiment, the storage device 230 is not a CD-ROM device or a DVD device.

Generally, the exact physical components used in a client device 110 will vary in size, power requirements, and performance from those used in the application server 130 and the database server 140. For example, client devices 110, which will often be home computers, tablet computers, laptop computers, or smart phones, will include relatively small storage capacities and processing power, but will include input devices and displays. These components are suitable for user input of data and receipt, display, and interaction with notifications provided by the application server 130. In contrast, the application server 130 may include many physically separate, locally networked computers each having a significant amount of processing power for carrying out the asthma risk analyses introduced above. In one embodiment, the processing power of the application server 130 provided by a service such as Amazon Web Services™. Also in contrast, the database server 140 may include many, physically separate computers each having a significant amount of persistent storage capacity for storing the data associated with the application server.

As is known in the art, the computer 200 is adapted to execute computer program modules for providing functionality described herein. A module can be implemented in hardware, firmware, and/or software. In one embodiment, program modules are stored on the storage device 230, loaded into the memory 215, and executed by the processor 205.

III. Dashboard

Figure 3A:
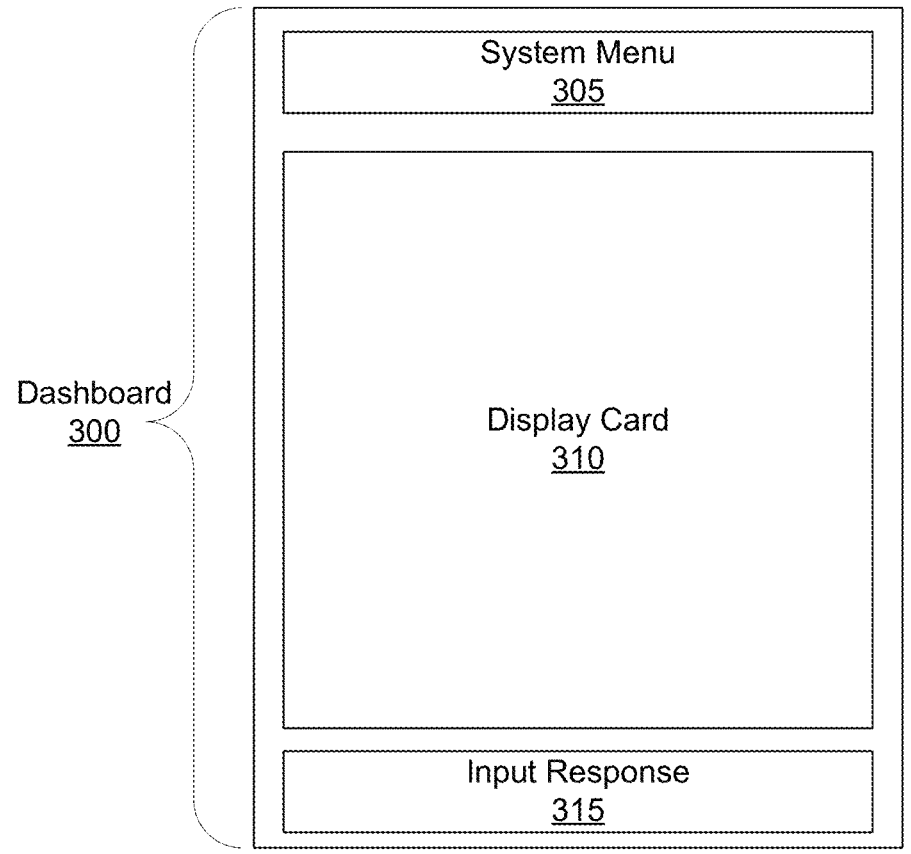
FIG. 3A shows a dashboard of a client application that allows a user to interact with an asthma analytics system, according to one embodiment.

The dashboard, for example dashboard 300 illustrated in FIG. 3A, allows users to interact with the asthma analytics system 100. The dashboard 300 provides a means to transfer information on a user-to-user (e.g., patient 111 to provider 112) or user-to-system/system-to-user basis. Dashboards 300 are accessed through the client application 115 on the client device 110 and provide a mechanism for both patients and healthcare providers to monitor medication rescue events, exchange personalized patient healthcare information, and receive notifications such as asthma rescue event risk notifications. Patients may communicate with other health care providers and other patients through the dashboard 300, for example, to discuss and share information about asthma, medication usage, or asthma management. The ability to share asthma healthcare information may give patients or healthcare care providers experiencing a similar issue a way to share individual perspectives.

The dashboard 300 also allows authorized health care providers 112 to access a list of patients to view, annotate, update, interact with, and export information about asthma patient and community data and statistics in various demographics or geographic segments. Using the dashboard 300, healthcare providers are able to monitor patients individually or in aggregate, to receive and provide feedback on how their associated patient populations are responding to asthma management guidance. A healthcare provider who has access to individual or multiple patients has the ability to establish notification thresholds, set parameters for the notifications, and receive notifications when patients' event history matches certain conditions (e.g. rescue event). Additionally, the dashboard 300 can receive and display regular reports of event patterns for specific demographic generated by the asthma analytics system 100.

The dashboard 300 presents a variety of information including tabular data, graphical visualizations, and analyses to users through display "cards" 310. Display cards 310 are conformably suited to smaller displays typical of portable client devices 110, for example mobile phones or tablets, and include "bite size" pieces of information that mimic the simplistic organizational style found in baseball cards. The dashboard 300 may also include a system menu 305 that allows users to navigate through different categories of healthcare information.

Notifications provided by the application server 130 are related to the display cards 310. Generally, notifications include not only information to be presented to the user through the application 115, but also parameters for specifying which display card 310 is to be used to display the contents of the notification. Any information pushed/pulled from the application server 130 may be associated with one or more cards. For example, a notification can be pushed to the patient based on the outcome of an asthma risk analysis. The dashboard 300 will process the notification and determine which card/s to use to present the information in the notification. Continuing the example, the recipient of the notification may make a request to pull data from the application server 130. The application server 130 provides the requested data in another notification, and the dashboard 300 then determines which display card 310 to display the requested information.

To interact with information presented, some display cards 310a include a input response 315 area. For example, in the display card 310b illustrated in FIG. 3B, a patient may scroll up or down in the input response 315 area to select a controller medication used to manage asthma or select the "next" to move to an additional display card 310.

The dashboard 300 may provide a variety of different display cards 310, which may be organized into categories. An information card type includes cards that display data. Information cards may, for example, display medication rescue events, statistics, and maps including both patient data and community data. Information cards are further sub-categorized into event, trend, education, and alert display cards.

Event cards include data relating to rescue medication events, such as a list of historical medication rescue events for a specific patient, or patient rescue event data overlaid on a geographical map for a specific provider.

Figure 3B:
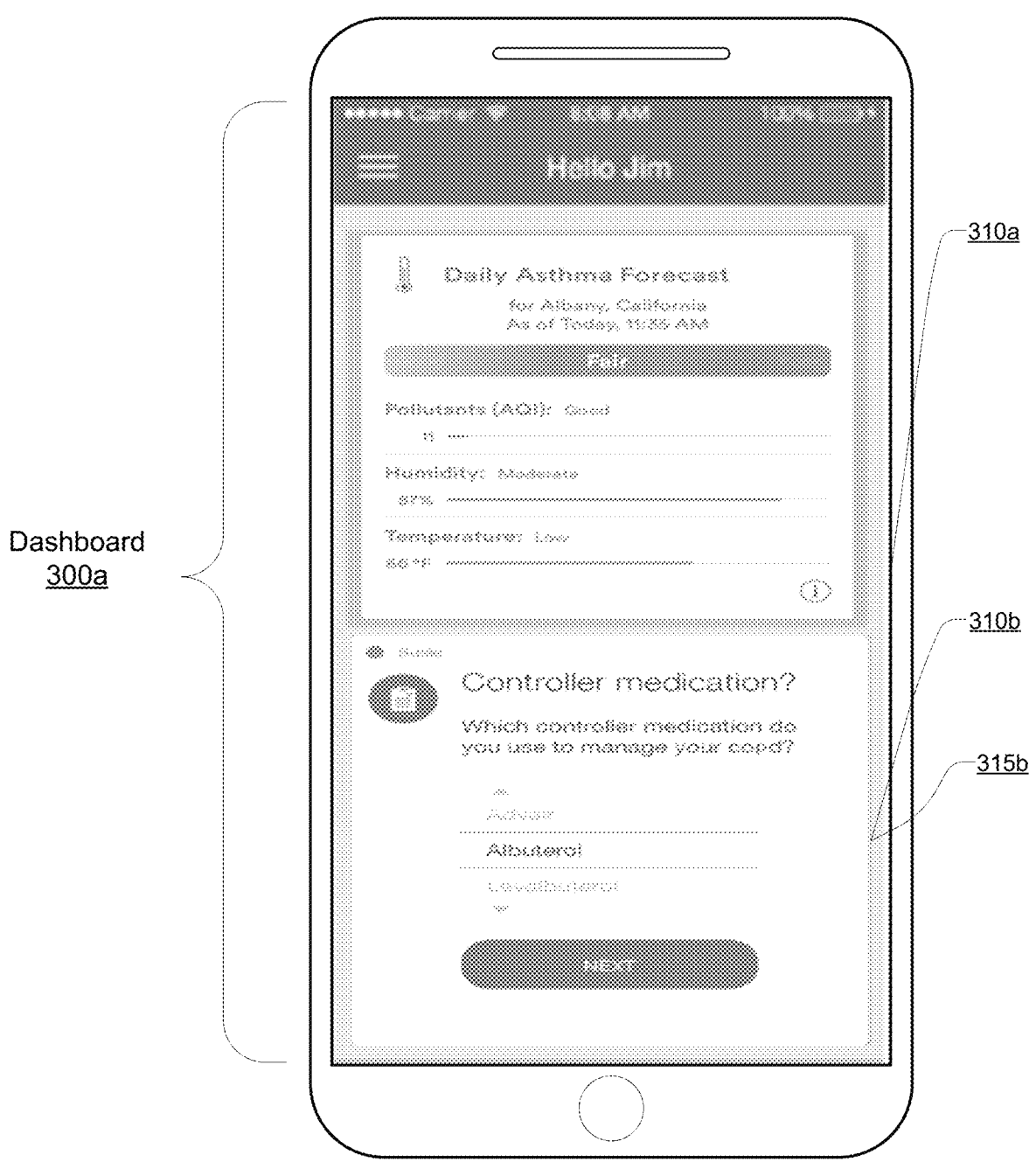
FIG. 3B shows an example card displayed within the dashboard of the client application, according to one embodiment.

FIG. 3B illustrates an example display card 310a sent by the notification module 645 (discussed below), which is sent based on the determination of a risk score by the data analysis module 131. The display card 310a highlights patients information obtained from the input values used to determine the risk score, for example the patient's current geographical location as specified by their device 110, and environmental information. The display card 310a also includes a risk categorization based on the risk score, in this case "fair" which may represent a medium risk categorization.

Another event card may display an example medication usage report including a map of the location of a rescue usage event, environmental conditions at the location, and an input response area 315 for the recipient to add triggers for the rescue usage event. Another event trend card may display rescue device usage for the previous week including a total number of uses for the time period and a number of uses for each day.

A trend card includes statistical information presented using a graph or a chart designed for clear comprehension by the recipient. Examples of trend cards include plots of asthma rescue events over various time periods, time of day trends, days of week trends, and trigger trends.

An education card includes information meant to educate the recipient. Education cards provide general disease information and tips for patients to reduce their risk of rescue events. Some education cards may require an input response 315 to allow recipients to specify whether the information provided is relevant or interesting for use in serving future cards.

Alert cards notify users of important information including informing a recipient that they are at risk for an event and/or that data has not been received from a device over a recent time period. Other alerts may include an alert that a setting on the client device is preventing data syncing (e.g. Blue tooth is turned off) or that a patient's asthma risk score has changed.

A survey card type solicits a user response by presenting yes/no, multiple choice, or open-ended questions for the user to respond to. For example, a healthcare provider or the asthma analytics system 100 may send a survey card with an asthma-related questionnaire to a patient 111 to determine a level of disease control for a specific patient. Additionally, a survey card may request the type of controller medication that the patient 111 uses to treat asthma symptoms. Generally, survey cards provide the application server 130 with data that may be missing from a patient's medical history or patient profile (as introduced above), and/or provide an update to potentially outdated information. One or more survey cards may be used to complete the patient enrollment process and create a patient profile for storage in database server 140. For example, when a patient 111 initially enrolls in the asthma analytics system 100, a push notification will be triggered by the application server 130 prompting the patient 111 to create a patient profile.

Example of survey cards may include a survey question asking whether a patient has made any emergency room visits as a result of asthma rescue events, information about the patient's controller medication, how many times the patient used their rescue medication to control an event, and what their controller medication daily schedule is. Survey cards may also ask about a patients asthma triggers, such as whether pollen is a trigger. Some survey cards may ask a patient to rate their general quality of life on 5-point Likert scale, to rate their quality of sleep, to rate their ability to be active over last 7 days, and so on. Other survey cards ask whether the patient feels better or worse than yesterday, whether the patient has had to go to emergency room or hospital in last 12 months for a rescue event and so on.

In some instances, patient behavior or sensor-reported event information that is inconsistent with existing patient information may trigger the sending of a survey card in order to resolve ambiguity as to the patient's circumstances. For example, if the patient is experiencing a greater-than-expected count of asthma events, the survey card may request information about the type of medication the patient has currently listed on their medicament device 160, in order to verify that the correct medication is being used. Another example includes if the reported information about controller medication use indicates that the patient is only using the controller medication one time per day but their adherence plan indicates they are supposed to be taking their controller medication twice per day, system 100 could send a notification asking if the patient needs to change their adherence plan.

In some instances, patient behavior or sensor-reported event information that is inconsistent with existing patient information may trigger the sending of a survey card in order to resolve ambiguity as to the patient's circumstances. For example, if the patient is experiencing a greater-than-expected count of asthma events, the survey card may request information about the type of medication the patient has currently listed on their medicament device 160, in order to verify that the correct medication is being used. As another example, if the reported information about controller medication use indicates that the patient is only using the controller medication one time per day but their adherence plan indicates they are supposed to be taking their controller medication twice per day, system 100 could send a notification asking if the patient needs to change their adherence plan.

Navigation cards represent actionable data or messages that, upon user interaction, may redirect the user to another screen or card that is part of the dashboard 300. For example, if a patient wants to share information or request specific medication plans for controller medications with a physician, a navigation card would be used to facilitate the sharing of information or enrollment in controller adherence plan. Additionally, navigation cards allow users to update information surrounding medication rescue events.

Adherence cards are designed to encourage a patient to continually use their controller medication on schedule over different periods of time. Adherence cards may indicate a "streak" or continuous run of on-time controller medication events, a better performance in aggregate even if not streak has been Additionally, a survey card may inquire as to the patient physical state in response to recording a significant number of rescue events within a threshold period of time of each other. Controller medication events may be represented as graphs to illustrate when the patient 111 did and did not take their controller medication on time during various periods during the day, as prescribed by their health care provider 112. Cards may also detail a daily schedule for controller medication and an indicator for displaying whether the scheduled dose has been taken. For example, a red "X" may indicate the scheduled dose has not been taken, but a green check mark or a different symbol may indicate that the scheduled dose has been taken.

Setup cards guide recipients in associating sensors with client devices 110. Setup cards may guide pairing a sensor to a client device 110 using Bluetooth, prompt the recipient to initiate the pairing process or prompt the user to select a sensor device for pairing, or notify the user that the sensor is paired.

In some embodiments, the dashboard may present a user interface. The user interface may illustrate a list of rescue events, responsive to the user's selection of the "View Timeline" input response area 315c. The list displays rescue usage events over a time period and includes details such as date, time, number of puffs, and location. Recipients may edit rescue usage events and/or add additional details by selecting the edit interaction response areas. Some interfaces may present an event summary for a rescue usage event to the user. The event summary may be presented to the user in response to the user selecting the edit interaction response area of the user interface. From the dashboard, the user may also view and edit a medication list, detailing information such as medication type (rescue, controller, etc.), dosage schedule, and sensors.

IV. Event-Driven Asthma Risk Notifications

FIG. 4 shows an interaction diagram for providing asthma risk notifications based on medicament device monitoring, according to one embodiment. As an initial step, a patient interfaces with the dashboard 300 to initialize 405 a patient profile. Once the patient completes their patient profile, the client device 110 transmits the patient profile for use by the application server 130 and storage by the database server 140. Once a patient's patient profile is initialized 405, the application server 130 may begin to receive rescue medications events detected by the sensor 120 associated with the patient's medicament device 160. The initializing and completing of the patient profile is only performed once during the patient's first use of the medicament device.

Upon the sensor detecting 410 a rescue usage event, the patient device 111 collects and sends the rescue event data to the application server 130, where the event information is stored 415. Although only one such instance is shown in FIG. 4, this detection and storage process is generally performed with some frequency for many patients, generally upon detection of a rescue usage event. However, this frequency may differ from the frequency with which a risk analysis is performed.

Figure 5:
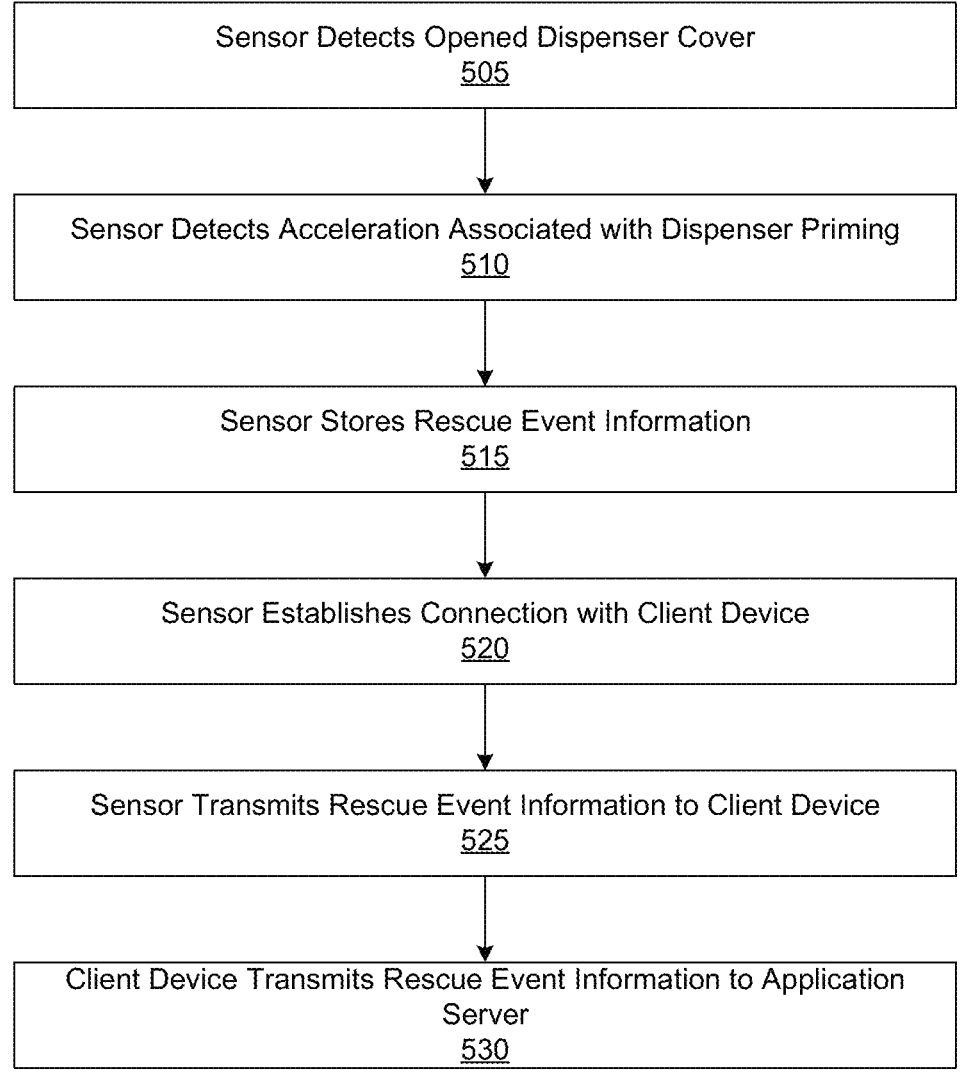
FIG. 5 is a flowchart for detecting a rescue medication event by an asthma analytics system, according to one embodiment.

Referring now to FIG. 5, the application server 130 generally receives a rescue event anytime the patient uses their rescue medicament dispenser 160 to relieve asthma-related event symptoms. As an example of the process for capturing such an event for a particular device 160/sensor 120 combination, at the start of symptoms, the sensor 120 may detect 505 whether a medication dispenser 160 cover is opened. When the medication dispenser cover is opened, the sensor 120 may detect an acceleration 510 associated with a priming of the dispenser 160. For some types of medicament dispensers, the "priming" includes activating a mechanism to release a dose of a medication from a packaging. In other types of medicament dispensers, the "priming" includes a rapid shaking of a medication canister.

After the priming action is detected, the sensor 120 is configured to store 515 data associated with the rescue event in active memory of the sensor 120. The rescue event data may include information that describes the time and date of associated with the rescue event, the status or condition of the medicament device 160 (e.g. battery level), the number of doses of medication remaining (before or after the event), self-test results, and physiological data of a patient being treated with the medicament device 160 as measured by the sensor 120. As soon as the sensor establishes a network connection with either the client device 110 or network 150, the sensor transmits 525 any locally stored rescue event data to the client device 110 or the application server 130. If the event data was transmitted to the client device 110 first, the client device 110 then transmits 530 the rescue event data to the application server 130 as soon as the client device 110 establishes a network connection with the network 150. Depending upon the implementation, either the client device 110 or sensor 120 will add the geographic location where the event took place to the event data transmitted to the application server 130.

Returning now to FIG. 4, upon detecting 410 a rescue usage event, event data is collected and stored 415. Upon receiving and storing 415 the receiving the rescue usage event data, the application server 130 may request further information from the patient describing the rescue usage event. To obtain the information, the application server 130 generates a push notification, including the questions to be asked, to be sent to the patient's client device 110. The client device 110 may present the push notification as a survey type card 310. The patient may respond to the request by providing inputs 315 in response to the survey card 310. Alternatively, the patient 111 may elect not to respond to the request. This is permissible, any gaps in information may be obtained through later push notifications, or upon entry by provider 112 after a meeting with the patient 111. In one implementation, the failure to receive the additionally requested data in response to request does not hold up the remainder of the analysis described in steps 425-445.

The information collected as part of the event or otherwise may identify 420, information pertaining to parameters that may have played a role in triggering the event, a location of the rescue event, a label (e.g., work, home, or school) for the location, a rating to signify the personal importance of the location to the patient, and whether the use was preemptive (e.g., medication taken prior to exercising) in addition to any other relevant information.

In addition to requesting additional event data, the application server 130 accesses 425 stored contextual data from the database server 140. Generally, contextual data refers data other than event data, which includes but is not limited to: to atmospheric conditions, weather conditions, patient data recorded from past rescue usage events, and any other considerations that are not directly detected by the medicament device at the time of the rescue usage event. By contrast, event data refers to any parameters related to the rescue event and reported by the medicament device, such as medication dosage, the time of the event, the location of the event, and relevant adherence data. Both forms of data may include temporally-current information as well as stored historical data. Accordingly, as part of obtaining the contextual data, the application server 130 also accesses historical rescue usage event data for the patient 111. This historical data can include all of the data from any past controller or rescue medication event data from the patient's history over a variety of windows of time in the past, and each historical event may include all of the same items of information as was reported 410 for this event along with any data collected upon follow up thereafter.

However, note that in the following description, such as in FIGS. 6A and 6B, in some instances contextual data 635 and historical data 620 are represented separately. The contextual data 635 refers to geographic and regional information relevant to the current event or current location of the patient's client device 110, whereas historical data 620 refers to geographic, regional, and event information from previous rescue usage events from the same or different patients.

IV.A. Asthma Prediction Model Overview

Figure 6A:
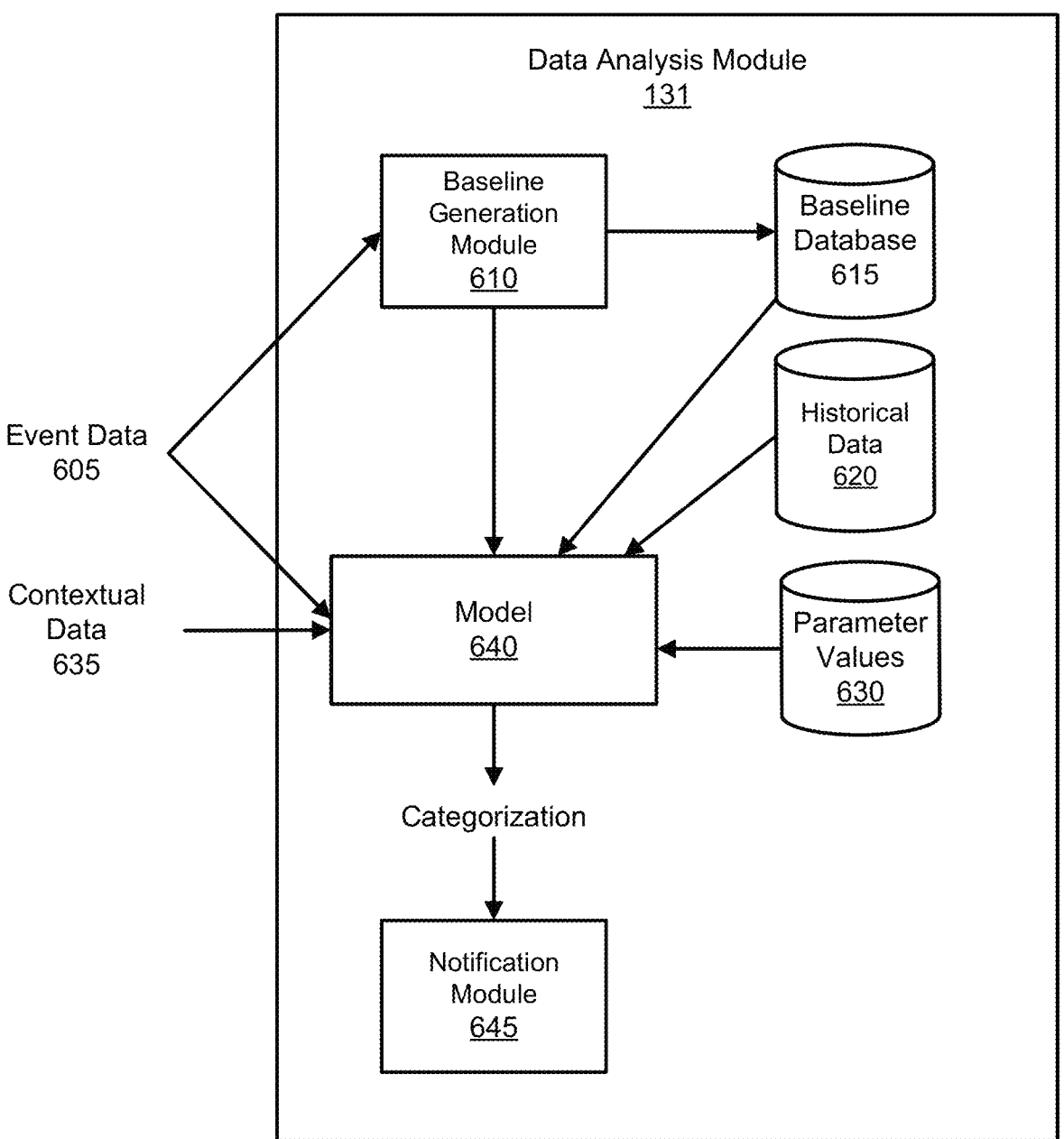
FIG. 6A is a block diagram illustrating the modules within the asthma risk score module, according to one embodiment.

FIG. 6A is a block diagram illustrating the logical components that carry out the functions of the data analysis module 131, according to one embodiment. The asthma analytics system 100 includes, on the application server 130, a data analysis module 131 that analyses the variety of data collected by the system, introduced above and discussed further below, to perform 430 risk analyses for patients upon occurrence of a triggering condition. These risk analyses are used to generate notifications that are specifically configured to be sent to a patient in a sufficiently timely manner to hopefully avoid the occurrence of an asthma event that would necessitate usage of their rescue inhaler.

In order to perform a risk analysis, a model 640, such as a mathematical function or other more complex logical structure, is trained using historical event data and historical contextual data to determine a set of parameter values that are stored in advance and used as part of the risk analysis. Training is discussed with respect to FIG. 6B in Section IV.B below. Parameter values 630 describe the "weight" (or critical value or other similar quantity, depending upon the modeling technique used) that is associated with at least one of the input values. Input values refer to numerical or categorical values of the parameters of the model 640, where the input values vary between patients over time.

Briefly, the risk analysis is performed by inputting aspects of a user's rescue inhaler usage events 605, 620 and the other contextual data 635, 620 as input values to the model's 640 function and parameters values 6430 and determine a numerical risk score. Generally, the contextual data collected for use as the input values may be gathered automatically based on device or other third party data reporting, manually provided by a patient and/or provider, or otherwise obtained. Risk scores are numerical values, generated by the model 640, that characterize the likelihood that a patient experiences an asthma rescue usage event given event data 605 and contextual data 635. The risk score may then be used to designate a risk categorization for the user that is particular to their current context at that moment in time, and either or both may be provided to the notification module 645.

The risk analysis may be triggered by a triggering condition, which itself may be automatically scheduled, manually set, and/or occur responsive to particular event or contextual information. Examples of triggering conditions include but are not limited to: a change in an input value, a result of the occurrence of a rescue event, or a conclusion of a time interval.

As part of the model 640 training process and during model use, the module 131 generates a baseline for a patient, generally on a periodic basis, where the baseline is used in other functions of the risk notification process. To do this, event data 605 is received by the baseline generation module 610 and is used to generate the baseline, which is then stored in the baseline database 615 for later. This process of generating a baseline generally occurs at specified frequency regardless of the occurrence of events or triggering conditions that might otherwise trigger system action. The methodology for generating the baseline is further described below in reference to FIG. 6C-6D below.

IV.B. Model Training

Figure 6B:
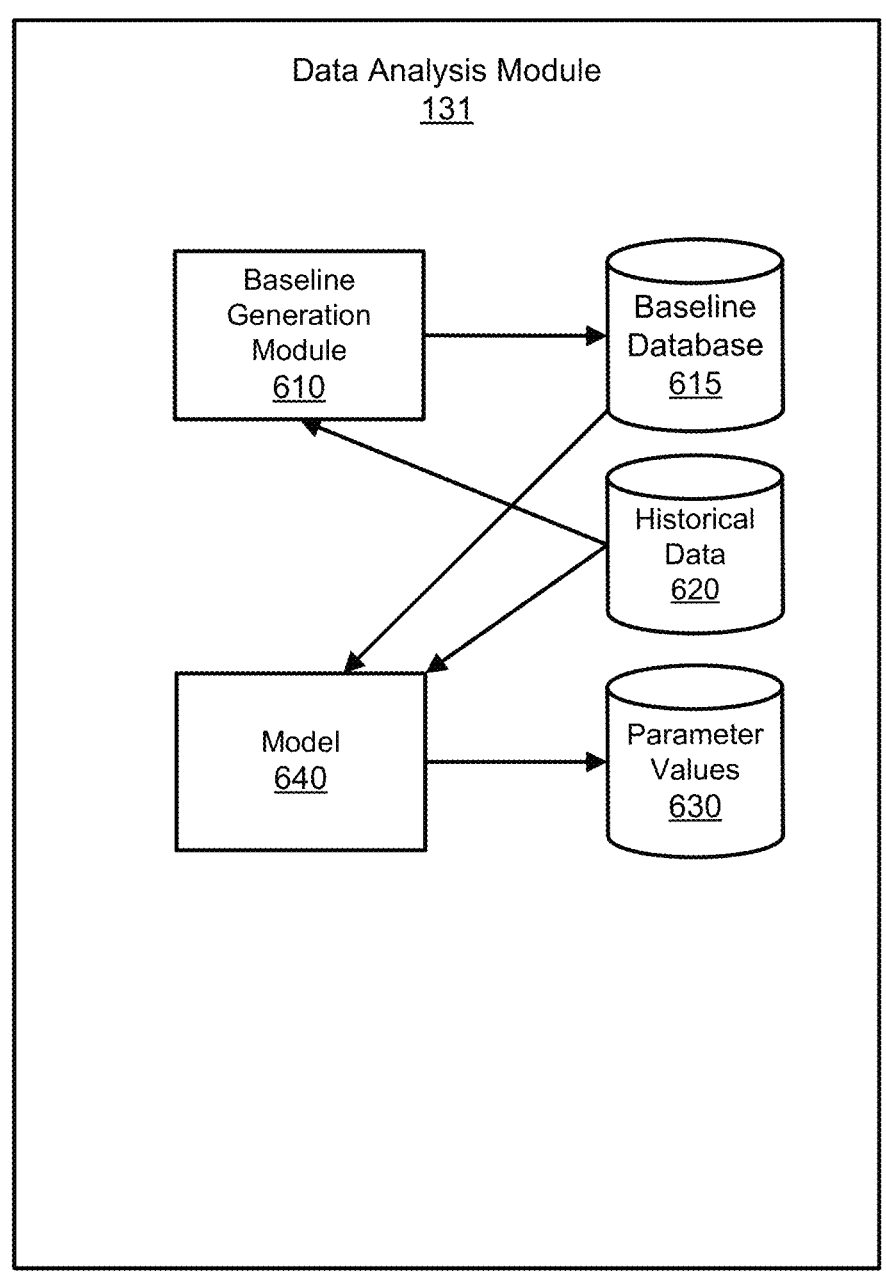
FIG. 6B is a block diagram illustrating the training modules implemented by the asthma risk score module, according to one embodiment.

With regard to model training and FIGS. 6B and 6C, the model is trained on labeled historical data, where historical event and historical contextual data associated with a prior day is associated with a labeled indication of whether that day was associated with high risk or low risk. This determination for the label of high or low risk is determined based on whether the events associated with the day exceed the baseline threshold for that day.

FIG. 6B is a block diagram illustrating a logical architecture for training the model, according to one embodiment. To create the data set used to train the model, the accessed historical data are aggregated/segmented on a per day basis, and input values for the various parameters are identified. Generally, each day's worth of information is associated with one training sample. Air quality and weather data may be obtained from National Oceanic and Atmospheric Administration (NOAA) and Environmental Protection Agency (EPA) historical data sets.

To create the label for each training sample, baseline thresholds are established for each day and the model 640 determines whether the baseline threshold is exceeded for each day based on the number of rescue usage events for that data. A full description regarding the determination the baseline threshold is discussed with respect to FIG. 6D in Section IV.D below, however generally the label associated with a given training sample represents a determination of whether that day was considered to be "high risk" or "low risk".

FIG. 6C is a diagram illustrating the method for training the model using the training data set 650, according to one embodiment. The model 640 is trained by determining parameter values (e.g., associated with each parameter, not shown) that best represent the relationship between the input values (cells of the table, represented by A) of the training samples 650 (each row of the table) and the labels of those samples (C). As introduced above, the model 640 is trained using some a function (B) or another more complex logical structure. In one embodiment, the model 640 is trained using a machine learning technique, examples of which include but are not limited to linear, logistic, and other forms of regression (e.g., elastic net), decision trees (e.g., random forest, gradient boosting), support vector machines, classifiers (e.g. Naïve Bayes classifier), fuzzy matching. An example model 640 trained using gradient boosting is described in Section IV.E below.

Once the parameter values are known, the model 640 may be used, as discussed in FIG. 6B by accessing the parameter values and the function specified by the model, and inputting input values for the parameters to generate a risk score.

IV.C. Input Parameters

The parameters incorporated into the risk score analysis can be categorized into several groups: historical patient parameters, current patient parameters, air pollutant parameters, and weather parameters. Historical and current patient parameters may be more broadly categorized as simply "patient parameters". Air pollutants and weather variables may be more broadly categorized as simply "environmental conditions parameters" The numerical values of the parameters are factored into the generated function in the form of input values, as described above. Further, from the parameters, the parameter values of the model are derived.

The historical patient features may include, but are not limited to: a cumulative patient history of rescue events over some period of time (pr_7_rscu_sum), a cumulative count of the days that the rescue unit has been in use (norm day), the disease type (disease_asthma), a record of rescue events occurring at night, and a controller medication adherence record (pr_sun_adh). The patient history of rescue events may include any relevant information pertaining to the categories mentioned above for any previous rescue events. The disease type describes the severity of the patient's asthma as well as their personal treatment regimen. The controller medication adherence record contains information for the patient's use of their controller medication (which may also be associated with a sensor unit 160). This determination is evaluated by observing instances where usage was prescribed, but not performed, instances where usages was prescribed and performed, and instances where usage was not prescribed and was performed.

Current patient features may include, but are not limited to: a current latitude (lat), longitude (lon), and location of a coordinate of the client device 110, and the current date (month, day_of_week). The current latitude and longitude are used to determine the patient's geographical location, from which information pertaining to the patient's environmental conditions can be determined. Current rescue event data may also include a difference between the number of rescue puffs taken versus the number prescribed, as well as a count of any rescue events that may have already occurred that day and information relevant to those events.

Air pollutant features may include information about concentrations (e.g., analog values), or more binary indications of presence or absence of pollutants. Examples of pollutants considered include, but are not limited to, ozone molecules (o3), nitrogen dioxide molecules (no2), sulfur dioxide molecules (so2), particulate matter of size 2.5 micrometers or less (pm25), particulate matter of size 1.0 micrometers or less (pm10), and the air quality index. Specific weather features may include temperature (drybulbfahrenheit), humidity (relativehumidity), wind speed (windspeed), wind direction (wind_direction_cat), station pressure (stationpressure), and visibility.

IV.D. Threshold Determination

As introduced above, baseline risk thresholds are used both in model training and risk score calculation. The baseline generation module 610 calculates the baseline risk threshold based on the total number of usage events over a specified prior time period preceding either the current day during which the risk is being calculated (for either labeling during training or during model use), or more generally during a time period preceding the time of a current/most recent rescue usage event.

In one example, the time period is a range bounded by the current day and seven days prior, exclusive (so, excluding the current day's data from consideration), however other time periods may be used. If there are not seven days' worth of data accumulated, for example due to a patient profile having recently been created or usage events not having been tracked during this time window, the baseline may instead be calculated based on the number of days for which data is available.

In one embodiment, the baseline risk threshold is set as a fraction (percentage) of the total number of usage events over the specified period, however in other embodiments, other functions of the total number of usage events may be used to determine the threshold.

FIG. 6D illustrates two example risk threshold determinations, and their use for determining the label for a training sample of the training data set, according to one embodiment. First, the total number of usage events from the preceding seven day period is summed and recorded. For both examples, this total is 30 events. Second, the risk threshold is determined as the number of events that is equal to 5% of the total, which in this case is 1.5 events.

In training, samples (the events and other data related to a day's events) are labeled as "1" or "0" where 1 indicates a high risk to the patient and 0 indicate a low risk. As this is historical data, this "assignment" of risk is based on the assumption that the more rescue usage inhaler events occurred for a user, the worse the patient's condition was, suggesting some complex combination of the input values of the parameters that caused the behavior to be worse than it was on other days. Thus, in the labeling scenario it isn't really a risk per se, so much as an occurrence that the model is seeking to identify in order to avoid in the future.

To assign the label, if the number of rescue inhaler usage events in a given day is greater than the threshold, here greater than 5% of the 30 events tallied over the last seven days, it is assigned a 1. Otherwise, it is assigned a 0. FIG. 6D illustrates both possible examples, in a case where 2 events are reported by the sensor 160 on a day, and in a case where 1 event is reported on the day. These definitive determinations allow the model, once trained to determine what combinations of input values kinds of events constitute a risk event and which kinds do not. The setting of the threshold based on a fraction of the prior period's events, as opposed to a fixed number of events, allows for greater flexibility and variability in tailoring the threshold to the patient's specific disease state. Specifically, if the patient's rescue inhaler usage is elevated over a number of days, then having the threshold be dynamic in this manner allows better identification of whether the parameters are (or are not) exacerbating the patient's condition. In one embodiment, the baseline risk threshold is set to 5% rather than some higher threshold such as 14% (representing a 1 day average out of a 7 day history) to account for right tailed usage patterns with asymmetric distribution due to frequent 0's and to ensure high risk categorizations of days with usage events greater than a median day yet below the 7-day average.

IV.E. Gradient Boosted Decision Trees Example

In one embodiment, the model 640 is a gradient boosting model. Generally, gradient boosting involves the use of an ensemble of weak prediction models, typically decision trees. In the case of decision trees, each tree is a weak learner of relatively shallow depth addressing only a handful of parameters. The training mechanism of the model 640 is an iterative functional gradient descent algorithm. That is, the algorithm optimizes a cost function over the parameter space by iteratively choosing a function (weak hypothesis) that points in the negative gradient direction. Stated differently, in each iteration of training the algorithm chooses the parameters for new trees so as to minimize the error identified by the cost function from the trees and parameter values of the prior iteration.

In one specific embodiment, the XGBoost set of algorithms and framework is used as the baseline of the model 650. One example model was run with the variables of XGBoost set such that max_depth=9, min_child_weight=1, gamma=0, learning_rate=0.1, n_estimators=1000, subsample=0.8, colsample_bytree=0.8, objective=binary:logistic, nthread=4, scale_pos weight, and seed=27. Additional details regarding the XGBoost algorithm can be found at http://xgboost.readthedocs.io/en/latest/python/pytho-n_api.html. Cross validation was performed on the data. For sake of convenience in the remaining description, this example is referred to as the XGBoost Example Model.

IV.F. Asthma Prediction Model Use

Returning now to FIG. 4, the application server 130 uses the trained model performs an asthma risk analysis 430 to determine the risk that a patient will experience an asthma event in the near future. This risk is embodied as a numerical score, but can also be processed into a risk categorization, such as whether the patient is within a high risk category, a medium risk category, and a low risk category. This information may be used, among other reasons, to attempt to effect a change in patient behavior to avoid the predicted event.

Referring now to FIG. 6A, the data analysis module 131 accesses input values to be able to use the model, where the input values are determined from any current rescue event data 605, historical rescue event data 635, current contextual data 635, historical contextual data 635, and the parameter values 630. The module 131 also determines or accesses a baseline risk threshold, depending upon whether a sufficiently current threshold is present in database 615. The model 640 uses these inputs to determine the risk score. As discussed above, the model 640 is trained on normalized risk values of 1 or 0, indicating whether particular prior days were or were not high "risk" for a patient. The numerical risk score generated by the model 640 will similarly be a normalized value between 0 and 1 inclusive. Thus, the numerical risk score represents the model's 640 determination about whether the current input values indicate that the patient is at high or low risk. Further, recall that the I/O labels were based not on whether the patient had a rescue inhaler use that day per se, but whether they exceeded the dynamic threshold, which in some cases is set based on whether they exceeded some fraction of their moving-window average over a prior time period. Thus, similarly the risk score output by the model also reflects not simply whether a rescue inhaler usage event will occur, but instead whether based on the input values the patient is expected to exceed their own moving window average as identified by the present baseline risk threshold.

Module 131 may further categorize the risk score is categorized as a high risk, medium risk, or low risk, or some other breakdown that contextualizes the risk score. As one example, scores considered to be low risk range between 0.0 and 0.1, medium risk range between 0.1 and 0.8, and high risk range between 0.8 and 1.0.

IV.G. Asthma Rescue Event Risk Notifications

The notification module 645 generates 435 a risk score notification including any one or more of: the categorization, the risk score, potential causes for the risk score, and options that the patient can take to prevent the occurrence of another rescue usage event under these circumstances. As discussed above, the application server 130 generates 435 a risk score notification for one or more of: the patient 111, their healthcare provider 112, and/or any other authorized individuals.

The risk notification may include a wide variety of informational content, including the risk score, the categorization, and any of the input values from any of the parameters of the model 640.

The risk notification may also be comprised of a recommendation regarding how to prevent future rescue inhaler events based on the parameters responsible for the change in the risk categorization. For example, the recommendation may include following the adherence schedule more closely, increasing the dose or usage of a controller medication, avoiding that geographical region altogether, or limiting exposure to areas with similar environmental conditions.

Additionally, a patient 111 may be provided a geographical map with pinpoints of all of their medication rescue event locations that have occurred in the last year. As another example, a patient 111 may be provided with a geographical map include where event 410 took place, along with pinpoints of all medication rescue events that have occurred in the nearby geographical area either that day or within a threshold period of time, to indicate recent patterns in medication rescue events for that area. As another example, the healthcare provider 112 of the patient 111 may be presented with medication rescue event data from their patients 111 from that day or a recent period of time to help the provider 112 identify medication rescue event trends.

The risk notification may also be delivered in many other situations which depending upon the implementation may be based on triggering conditions, or may be sent to the client device according to some other mechanism. For example, if a patient's current condition worsens due to changes in patient parameters (e.g., decreased patient controller medication adherence trend) or environmental condition parameters (e.g., low concentrations of ozone, greater amounts of pollutants in the air, or higher humidity) an updated risk notification is delivered to the patient 111. Alternatively, if a patient's current condition improves due to similar changes, an updated risk notification may also be delivered. Risk notifications may also be delivered at a patient's request, for example due to a verbal request for local asthma conditions from a third party device (e.g., Google Home™ or Amazon Alexa™).

As described above, generally risk notifications are delivered through the client device 110, however in other embodiments, in the event of improved or worsened conditions, risk notifications may be delivered as an SMS notification, an email notification, a notification from an embeddable widget with local asthma conditions, or notifications from various IFTTT applets (https://ifttt.com/).

V. EXAMPLES

V.A. Example 1

FIG. 7A characterizes the training data set, by indicating the percentage of days that were labeled as 1's and the percentage of days that labeled as 0's. Additionally, the graphs demonstrate the increase in the number of days categorized as high risk based on a baseline risk threshold that includes the 5% factor as discussed above versus a baseline risk threshold that does not. The dataset is represented per user (patient) per day, joining Propeller Health's™ patient inhaler data to air quality and weather data from the NOAA and EPA historical data sets ranging from Apr. 30, 2012 to Apr. 30, 2017. For users lacking location information, the discrepancies were filled using the most recently logged location during that 24 hour period. If no location was logged during that 24 hour period, the day's data was removed from the dataset. The total dataset comprised 5,309 users and 720,812 user days, of which 15% were categorized as high risk (or 1's). Low risk days are categorized as 0's. Of the total dataset, 5,202 users and 178,920 user days were selected for the training set. To improve model training, sub-sampling techniques have been used to balance the training set (e.g. an equal number of events labeled 0 and 1). The test set comprises 3,982 users and 35,848 users and remains unbalanced with 15% of the user days being categorized as high risk.

The data indicated that, when using the XGBoost Example Model, 98% of days having 1 event were classified as high risk, compared to the 75% of high risk days under a no-% threshold model. This significant improvement in accuracy reduces the possibility that the device fails to recognize any given high risk rescue usage event. In addition, the XGBoost Example Model now addresses the issues concerning the right tailed distribution of individual patient daily usage events, discussed above.

V.B. Example 2

FIG. 7B describes the reasoning behind setting the baseline risk threshold as percentage (e.g., 5%) of the previous time period sum of rescue usage events. A previous model (herein referred to as "V1") has categorized 26% of events as high risk (i.e., label "1") provided the most optimal combination of AUC Scores, accuracy measurements, and sensitivity and specificity readings (Sample set was based on earlier data with 30,790 patient days of data). Other similar iterations of similar models also categorized 20% of greater of patient days as high risk. This was unrealistic relative to surveyed and separately identified measurements of what percentage of most patients days are high risk. When designing the training data set for the XGBoost Example Model, the 5% threshold was found to better represent the conventionally determined rate of high risk days (less than 5%, as indicated by FIG. 7a). To train the XGBoost Example Model, a training data was built comprising 5,202 users and 178,920 user days. To improve model training, sub-sampling techniques have been used to balance the training set (e.g. an equal number of events labeled 0 and 1).

V.C. Example 3

FIG. 7C illustrates the same performance metrics for the XGBoost Example Model. The training and test data sets are the same data identified in FIG. 7A. These performance metrics suggest a decline in efficacy from the measurements of the V1 model, however the XGBoost Example Model addresses deficiencies of the V1 model. Part of the decrease in specificity can be attributed to a significantly larger amount of low risk days than high risk days. Only 15% of events of the test set of the XGBoost Example Model were high risk, compared to 85% of low risk events. Comparatively, the V1 test set was only 78% low risk events. Additionally, the XGBoost Example Model considers additional parameters in the performance of its risk analysis and risk categorization relative to the V1 model.

V.D. Example 4

Figure 7D:
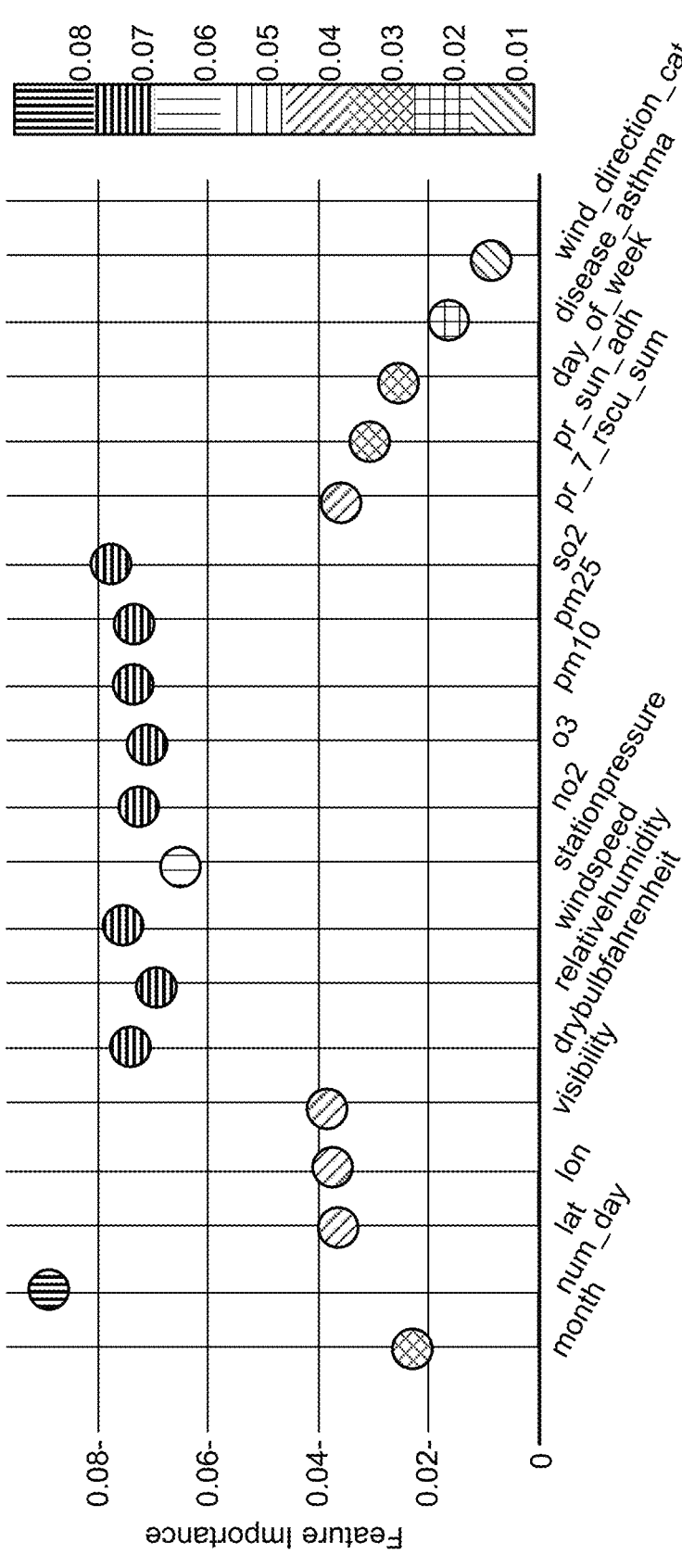
Figure 7E:
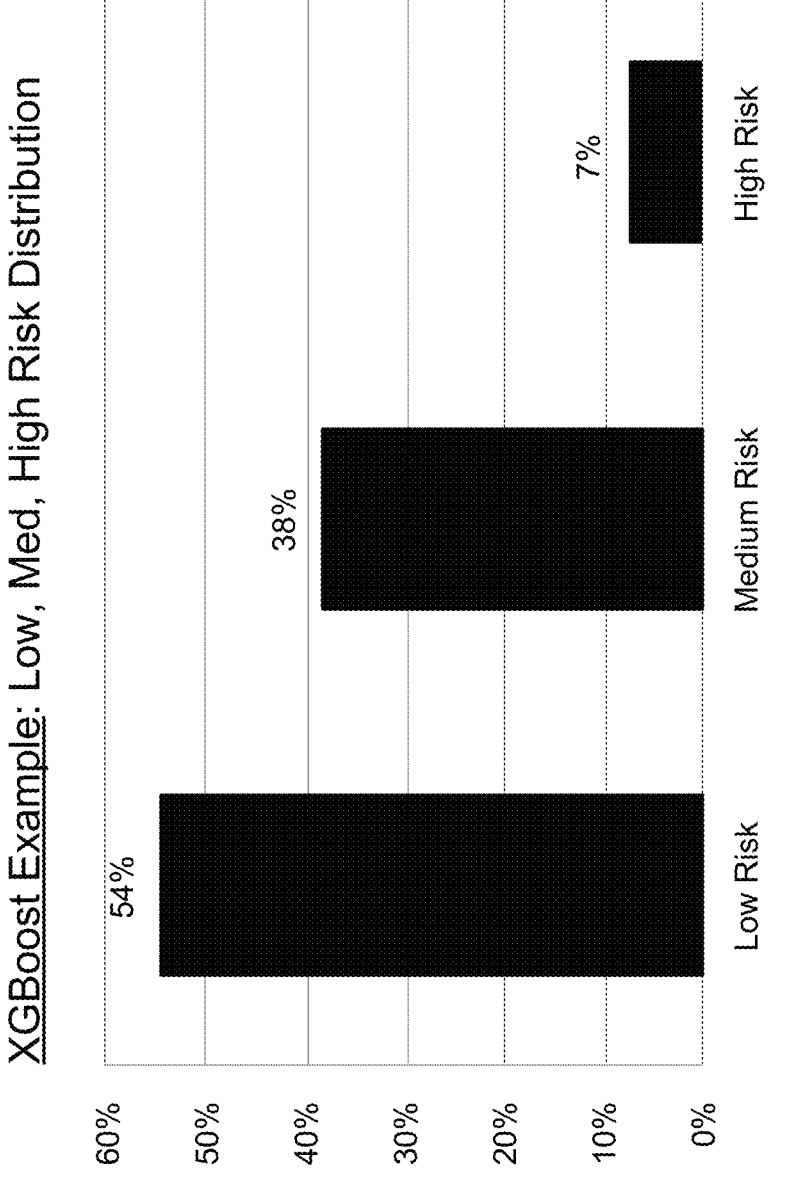

FIG. 7E displays a distribution of days from the test set categorized as high risk, medium risk, and low risk by the XGBoost Example Model. Days considered low risk make up the majority of the test set at 54%, followed by days considered medium risk at 38%, and days considered high risk at 7%. This risk category distribution is broadly consistent with the categorizations generated by the V1 model, wherein low and medium risk predictions far outnumbered the high risk predictions. Specifically, in the V1 model, low risk predictions accounted for 49% of the test set, medium risk predictions accounted for 32%, and high risk predictions accounted for 20%.

V.E. Example 5

Figure 7F:
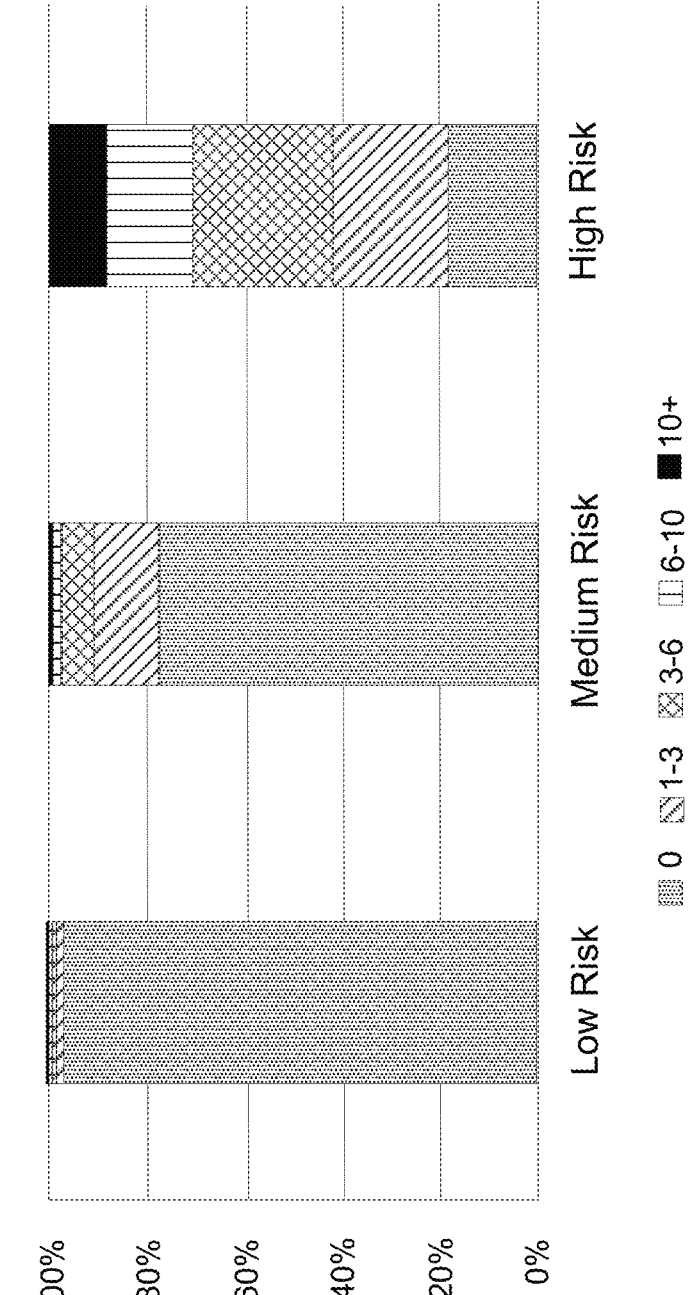

FIG. 7F breaks down the distribution of rescue events, representing the risk predictions by daily rescue event totals, based on the test data set for the XGBoost Example Model described above. Within days categorized as low risk, the vast majority of days had 0 events, but there were rare instances where days recorded a greater number of events. Within the medium risk category, the majority of days had 0 events, with a larger amount of days recording 1-3 rescue events and 3-6 rescue events. As seen in the low risk category, there were rare instances of days recording a greater number of events. Within the high risk category, there was a smaller number of recordings with 0 events compared to the previous categories, but larger number of recordings within the ranges of 1-3, 3-6, 6-10, and 10+ events within a day. Similarly to the data in FIG. 7E, the prediction trends from the XGBoost Example Model follow the same general distribution as the V1 model, with larger amounts of days recording 6+ events categorized as high risk.

V.F. Example 6

FIG. 7G describes the risk score variance across the majority of users in the XGBoost Example Model. The same test data set described above was used to perform the analysis. Within the test data set approximately 10% of the patients were positively diagnosed with COPD. Patients considered in the test set all had greater than 5 days' worth of accumulated data. Only 1% of users found 90% of their days to be categorized as high risk, only 4% of users found 90% of their days to be categorized as medium risk, and only 5% of users found 90% of their days to be categorized as low risk. Comparatively, 89% of users found varying risk categorizations with no single risk category accounting for a majority as large as 90%. The prevalence of the varying risk categories, suggests that he model is highly sensitive to changes in parameter values, regardless of whether they are associated with contextual or event data. This is further proved by comparison to the V1 model, wherein 64% of users saw varying risk scores, since the V1 model accounted for fewer parameters and was less sensitive to changes in contextual data and event data.

V.G. Example 7

FIG. 7D diagrams a number of parameters of the XGBoost Example Model and assigns each parameter an importance score representing the importance of the parameter in the risk analysis determination. Determining the importance of the various parameters is completed during the training of the model, wherein the model determines the parameter values to associate with the parameters. As such, the training data set is consistent with the characterizations described in reference to FIG. 7A-7B. Based on the model parameters and test data, the most important parameter is the historical parameter, the number of days that a patient has used the Propeller Health™, with a score of 0.08. The most important contextual parameters are $SO_2$ concentration, wind speed, temperature, PM1.0, PM 2.5, $NO_2$ concentration, and $O_3$ concentration, all with scores of 0.07, and all of which were not considered by the V1 model.

V.H. Example 8

Figure 7H:
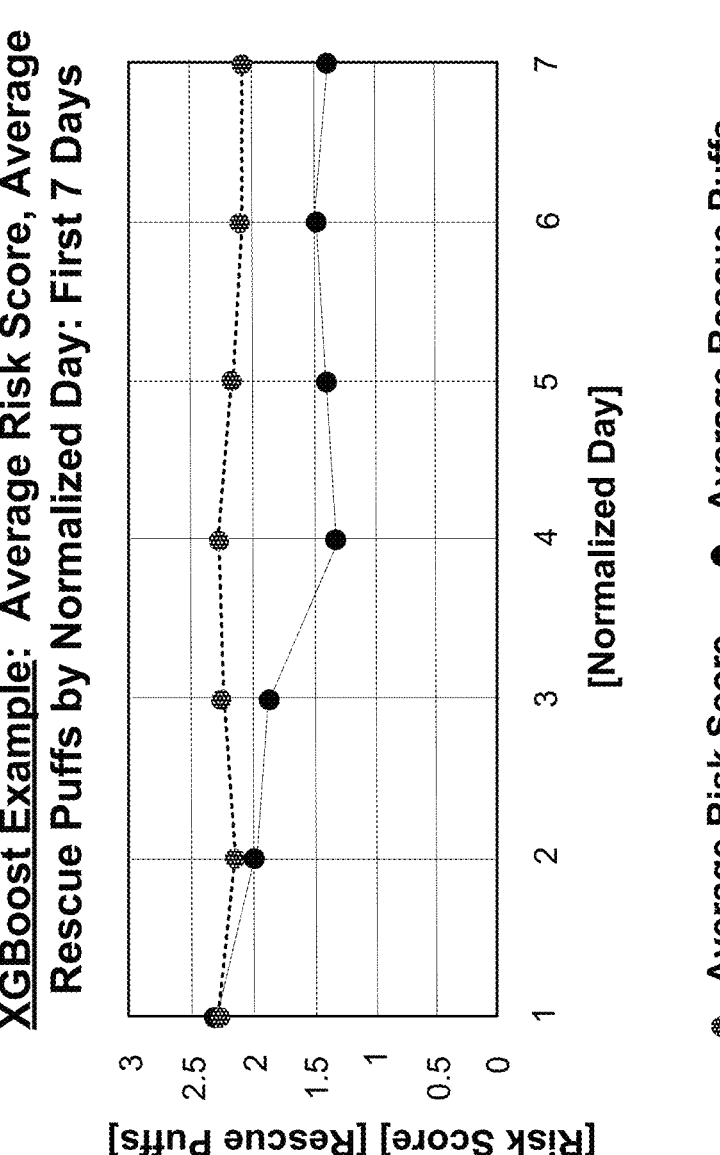

FIG. 7H describes the average number of rescue puffs over the first seven days a patient is being monitored using the Propeller Health™ system. The average number of rescue puffs was determined using the test data set described above. Given the improved dataset, the plot now more closely mimics Propeller Health's™ typical rescue curve, suggesting an improvement in the XGBoost Example Model over V1. Further, it shows that monitoring does lead to a marked improvement in rescue inhaler usage within that first week's time period, suggesting that monitoring and concordant notifications as described herein can help reduce patient's use of their rescue inhaler.

V.H. Example 8

Figure 7I:
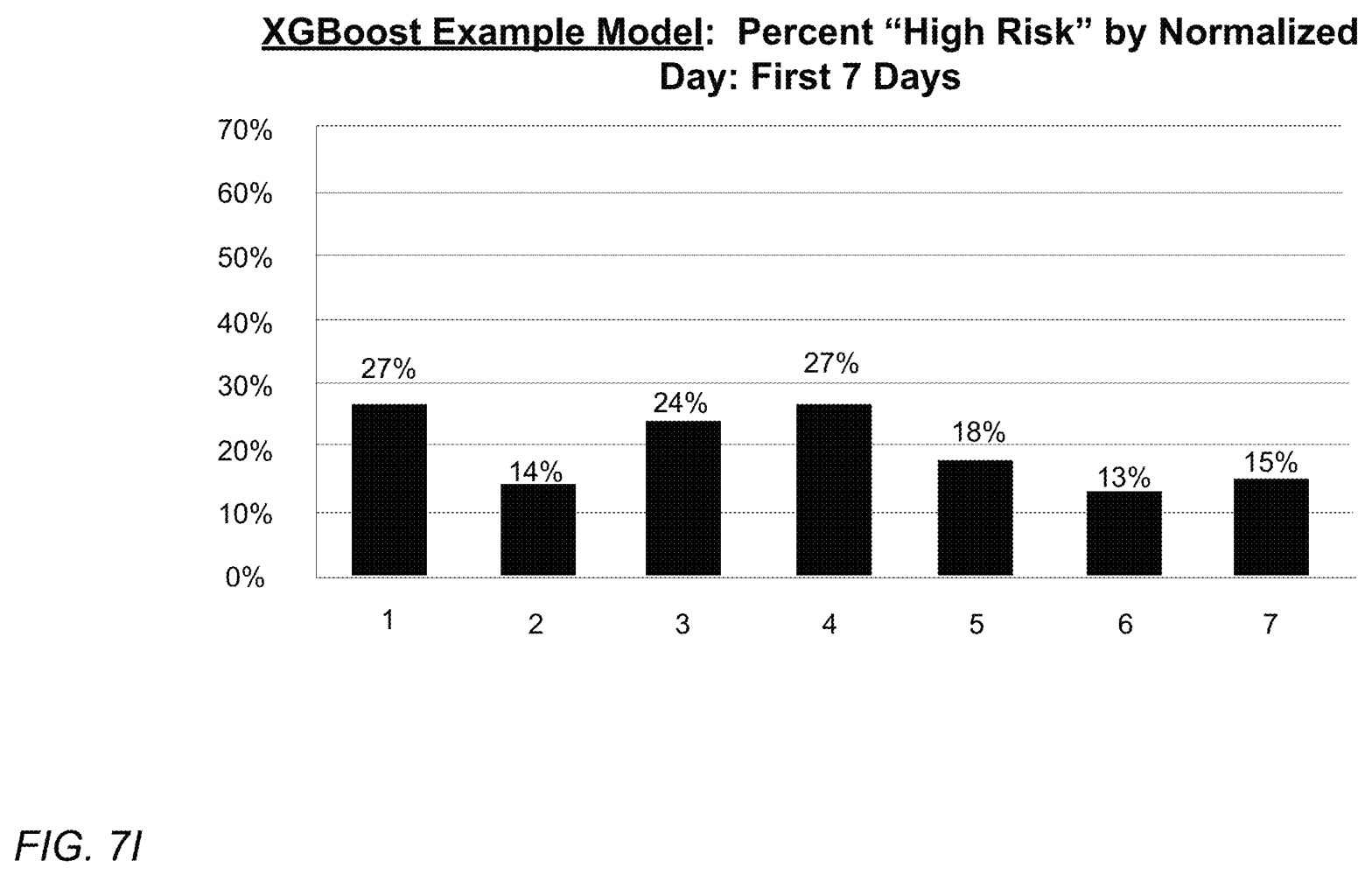

FIG. 7I further characterizes the data from the average first 7 days of the training data set, describing the amount of user's who were considered to be at high risk on each of the first 7 days. Overall each day represented a decrease in the percentage of high risk users compared to the V1 model, suggesting an improvement in the overall use experience during the first week. Specifically, on day 1, 27% of users in the XGBoost Example Model test set were considered high risk, compared to 35% of users in the V1 model. From days 2-7, respectively, 14%, 24%, 27%, 18%, 13%, and 15% of XGBoost Example Model users were categorized as high risk compared to the V1 model which respectively determined 37%, 38%, 31%, 31%, 30%, and 29% of users were categorized as high risk.

VI. Benefits

The asthma rescue event risk notifications provided to patients 111 and providers 112 convey many benefits. Patients are informed of their risk of an asthma rescue event in real time or near real time (on the order of seconds to minutes), and can take action to prevent that occurrence, for example by improving their adherence to their controller medication, staying away from geographic areas with adverse conditions (e.g., air pollution concentrations), adding or altering their prescribed medication regimen (such as an adjustment of dosage or the introduction of antibiotics or systemic cortiocsteroids), or scheduling an appointment with their doctor to address their recent spike in use of rescue medication which in turn would reduce the frequency of emergency room and hospital visits for the patient. Because the event data is automatically reported to the application server 130 without the need for patient input, the accuracy and quality of the event data is improved relative to manually-collected data by a health care provider 112 or other entity, and thus the accuracy of the conclusion for the risk of asthma rescue events is also improved.

Additionally, follow up notifications provided by the application server 130 including reports of nearby rescue medication events by other patients can provide patients with additional information about others who are suffering from similar issues and provide regional information relevant for the patient's decision-making. Follow up notifications can further encourage the user regarding progress on taking their adherence medication. Ideally such notifications will prevent the occurrence of asthma rescue events, thus preventing patient harm as well as hospital visits and their associated costs.

Health care providers informed of the risk of one or more of their patients' risk of asthma rescue events can similarly track the progress of their patients, and use the information to update their treatment regimen for each patient, schedule appointments with patients, and so on. For patients at high risk of a asthma rescue events, the notification may be a call to action for the health care provider to communicate with the patient and encourage them to seek medical treatment. Follow up notifications may provide information about regional effects (e.g., pollution), patient controller medication adherence, etc.

VII. Additional Considerations

Although the discussion above focuses on asthma specifically, all systems and processes described herein are equally applicable to chronic obstructive pulmonary disease (COPD) and chronic respiratory disease (CRD) generally, and consequently can also be used to assist in treatment of COPD and CRD, as well as asthma.

It is to be understood that the figures and descriptions of the present disclosure have been simplified to illustrate elements that are relevant for a clear understanding of the present disclosure, while eliminating, for the purpose of clarity, many other elements found in a typical system. Those of ordinary skill in the art may recognize that other elements and/or steps are desirable and/or required in implementing the present disclosure. However, because such elements and steps are well known in the art, and because they do not facilitate a better understanding of the present disclosure, a discussion of such elements and steps is not provided herein. The disclosure herein is directed to all such variations and modifications to such elements and methods known to those skilled in the art.

Some portions of above description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

While particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

What is claimed is:

1. A method comprising:
accessing a set of historical rescue inhaler usage events for a patient, wherein a historical rescue inhaler usage event is recorded when a rescue inhaler unit dispenses a rescue medication to the patient;
implementing a medicament device sensor attached to a rescue inhaler unit sensor configured to:
    monitor medicament usage of the rescue inhaler unit;
    record the set of historical rescue inhaler usage events; and
    establish a network connection with a client device, and transmit locally stored rescue event data to the client device such that the sensor and client device are paired using a passkey;
in response to accessing the set of historical rescue inhaler usage events:
    generating a push notification comprising a query to a client device associated with the patient;
    assigning a label representing a known risk score to each historical rescue inhaler usage event of the accessed set;
    determining a patient-specific baseline risk threshold for the patient based on a subset of the accessed set of historical rescue inhaler usage events that occurred within a period of time preceding a current day, wherein the patient-specific baseline risk threshold is determined based on a value representing a percentage of the subset of the rescue inhaler usage events;
    creating a training dataset comprising:
    the accessed set of historical rescue inhaler usage events, the label assigned to each historical rescue inhaler usage event;
    provider data including aggregated rescue medication event data, wherein the provider data is deidentified to protect privacy, and the patient-specific baseline risk threshold;
    training a machine-learned model to determine the risk score using the training dataset, wherein the machine-learned model is trained to determine the risk score based on a set of input values and the patient-specific baseline risk threshold, wherein the machine-learned model is trained based on an iterative functional gradient descent algorithm,
    wherein the algorithm optimizes a cost function by iteratively selecting parameters to minimize an error identified by the cost function; and
    in response to the risk score, updating a treatment regimen by altering a dosage of: antibiotics, corticosteroids, beclomethasone, budesonide, and fluticasone salmeterol or formoterol.

2. The method of claim 1, further comprising:
responsive to a triggering condition, accessing a set of parameter values for a model for predicting asthma risk;
accessing a set of input values for the current day, the set of input values comprising at least one historical patient parameter, at least one environment condition parameter, and at least one current patient parameter; and inputting the set of parameter values, the set of input values, and the patient-specific baseline risk threshold into the machine-learned model to determine the risk score for the current day.

3. The method of claim 1, wherein the machine-learned model is further trained to:

determine an expected count of rescue usage events for the current day based on the set of input values; and determine the risk score based on a comparison of the expected count of rescue usage.

4. The method of claim 1, wherein each parameter value of the set of parameter values is determined using a boosted gradient model.

5. The method of claim 1, wherein the risk score is a numerical value representing a likelihood that the patient will experience a number of rescue usage events on the current day exceeding the patient-specific baseline risk threshold.

6. The method of claim 1, wherein the patient-specific baseline risk threshold is periodically determined based on a prior period including events from a window of time preceding the current day.

7. A non-transitory computer readable storage medium storing instructions encoded thereon, that, when executed by a processor cause the processor to:

access a set of historical rescue inhaler usage events for a patient, wherein a historical rescue inhaler usage event is recorded when a rescue inhaler unit dispenses a rescue medication to the patient;

implement a medicament device sensor attached to a rescue inhaler unit configured to:

monitor medicament usage of the rescue inhaler unit;

record the set of historical rescue inhaler usage events; and establish a network connection with a client device, and transmit locally stored rescue event data to the client device such that the sensor and client device are paired using a passkey;

in response to accessing the set of historical rescue inhaler usage events, generate a push notification comprising a query to a client device associated with the patient;

assign a label representing a known risk score to each historical rescue inhaler usage event of the accessed set;

determine a patient-specific baseline risk threshold for the patient based on a subset of the accessed set of historical rescue inhaler usage events that occurred within a period of time preceding a current day, wherein the patient-specific baseline risk threshold is determined based on a value representing a percentage of the subset of the rescue inhaler usage events;

create a training dataset comprising the accessed set of historical rescue inhaler usage events, the label assigned to each historical rescue inhaler usage event, provider data including aggregated rescue medication event data, wherein the provider data is deidentified to protect privacy, and the patient-specific baseline risk threshold;

train a machine-learned model to determine the risk score using the training dataset, wherein the machine-learned model is trained to determine the risk score based on a set of input values and the patient-specific baseline risk threshold, wherein the machine-learned model is trained based on an iterative functional gradient descent algorithm, wherein the algorithm optimizes a cost function by iteratively selecting a plurality of parameters to minimize an error identified by the cost function; and in response to the risk score, update a treatment regimen by altering a dosage of:

antibiotics, corticosteroids, beclomethasone, budesonide, and fluticasone salmeterol or formoterol.

8. The non-transitory computer readable storage medium of claim 7 further comprising instructions that cause the processor to:

responsive to a triggering condition, access a set of parameter values for a model for predicting asthma risk;

access a set of input values for the current day, the set of input values comprising at least one historical patient parameter, at least one environment condition parameter, and at least one current patient parameter; and input the set of parameter values, the set of input values, and the patient-specific baseline risk threshold into the machine-learned model to determine the risk score for the current day.

9. The non-transitory computer readable storage medium of claim 7, wherein the machine-learned model is further trained to:

determine an expected count of rescue usage events for the current day based on the set of input values; and determine the risk score based on a comparison of the expected count of rescue usage.

10. The non-transitory computer readable storage medium of claim 7, wherein each parameter value of the set of parameter values is determined using a boosted gradient model.

11. The non-transitory computer readable storage medium of claim 7, wherein the risk score is a numerical value representing a likelihood that the patient will experience a number of rescue usage events on the current day exceeding the patient-specific baseline risk threshold.

12. The method of claim 1, wherein the treatment regimen further comprises:

restricting geographic areas with adverse atmospheric conditions and air pollution or scheduling an appointment with a health care provider.

13. The method of claim 1, wherein the medicament device sensor comprises a clock for recording the time and date of events.

* * * * *